US009434934B2

(12) United States Patent
Ho et al.

(10) Patent No.: US 9,434,934 B2
(45) Date of Patent: Sep. 6, 2016

(54) HEAT STABLE KERATINASE AND USE THEREOF

(71) Applicant: Academia Sinica, Taipei (TW)

(72) Inventors: Meng-Chiao Ho, Taipei (TW); Shih-Hsiung Wu, Taipei (TW); Wan-Ling Wu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 14/903,194

(22) PCT Filed: Jul. 17, 2014

(86) PCT No.: PCT/US2014/047052

§ 371 (c)(1),
(2) Date: Jan. 6, 2016

(87) PCT Pub. No.: WO2015/017137

PCT Pub. Date: Feb. 5, 2015

(65) Prior Publication Data

US 2016/0145593 A1 May 26, 2016

Related U.S. Application Data

(60) Provisional application No. 61/859,720, filed on Jul. 29, 2013.

(51) Int. Cl.

| | |
|---|---|
| ***C12N 9/58*** | (2006.01) |
| ***C12N 9/52*** | (2006.01) |
| ***C07K 14/39*** | (2006.01) |
| ***C12N 15/52*** | (2006.01) |
| ***C12P 21/06*** | (2006.01) |

(52) U.S. Cl.

CPC ................ *C12N 9/52* (2013.01); *C07K 14/39* (2013.01); *C12N 15/52* (2013.01); *C12P 21/06* (2013.01); *C07K 2319/00* (2013.01); *C07K 2319/02* (2013.01); *C07K 2319/21* (2013.01); *C07K 2319/22* (2013.01); *C07K 2319/50* (2013.01); *C12Y 304/21* (2013.01)

(58) Field of Classification Search

CPC ...................................................... C12N 9/58

USPC ................ 435/220, 252.33, 320.1; 536/23.2

See application file for complete search history.

(56) References Cited

U.S. PATENT DOCUMENTS

| | | | |
|---|---|---|---|
| 5,712,147 | A | 1/1998 | Shih et al. |
| 5,877,000 | A | 3/1999 | Burtt, Jr. |
| 2003/0108991 | A1 | 6/2003 | Shih et al. |

*Primary Examiner* — Tekchand Saidha

(74) *Attorney, Agent, or Firm* — Hsiu-Ming Saunders; Intellectual Property Connections, Inc.

(57) ABSTRACT

A fusion gene encoding *M. taiwanensis* WR-220 keratinase is disclosed. The fusion comprises: (a) a first DNA sequence encoding a protein secretion signal peptide, located at the N-terminus of the fusion gene; (b) a second DNA sequence encoding an inhibitory domain of *M. taiwanensis* WR-220 keratinase, linked in translation frame with the first DNA sequence; and (c) a third DNA sequence encoding a catalytic domain of *M. taiwanensis* WR-220 keratinase, linked in translation frame with the second DNA sequence, wherein the fusion gene is a non-naturally occurring chimeric DNA. Also disclosed are a method for preparation of the catalytic domain of *M. taiwanensis* WR-220 keratinase, and use of the *M. taiwanensis* WR-220 keratinase.

20 Claims, 10 Drawing Sheets

FIG. 8A SEQ ID NO: 3

0001 ATGTACCGTC TAGTTTGGAT CGCGCTGTTG TTGTTACTGG CATCCTGCGG
0051 AAACCGTGCG ACCCCCGACA ACCTAGCCCC GGTGCTAGGA CTGGATAACC
0101 CCAACGTTAT CCAGGGGCAG TACATTGTGG TCTACAAGGA TGATGCCAAC
0151 GTGCTGCCCA CCCTGCAAAG CCTGAAAGCC GCTTTAGATG GGGGTGTAAC
0201 CCTTCAGCGG GAACTGGAAA GCCTGGGGCT GGCACCCGAC GCCAGGGTTG
0251 AGCAGGTTTA CACCGCTGCT CTGCTGGGGC TTGCGGCCCG GCTATCACCC
0301 GAGAATTTAG CCGCGCTGCG GCAGGATCCC CGGGTGGCCT ACATCGAGGC
0351 CGACCAGGTC ATGAGCATCA GCGCCACCCA GACCGGTGCG ACCTGGGGCC
0401 TGGATCGCAT AGACCAGCGC ACCCTACCCC TCAGCGGTAC CTTCACCTAC
0451 AGCAACACGG GCAGCGGCGT GAACGCCTAC ATCATCGATA CCGGTATCCG
0501 GGTGAGCCAC AGCGAGTTTG GCGGTCGGGC CACGGCGGTT TTCGACGCTA
0551 TTGGAGACGG CCAGAATGGC AACGACTGCA ACGGCCATGG CACCCATGTG
0601 GCTGGAACGG TAGGCGGCAC GGTCTACGGC GTAGCCAAAA GCGTGCGGTT
0651 GTACGCGGTG CGGGTGCTTA ATTGCAGCGG CTCGGGCAGC AACTCGGGCG
0701 TAATTGCCGG GGTGGACTGG GTGCGGCAGA ATGCCCGGAG GCCAGCGGTA
0751 GCCAACATGA GCCTGGGTGG GGGGGCCTCG AGCGCCCTCG ATACCGCGGT
0801 CAATAACGCC ATCAACGCCG GGATTACCTT TGCCCTGGCC GCAGGTAACA
0851 GCAACCGCGA CGCCTGCCAG TTCTCGCCAG CCCGCGTCAC TGCAGGCATT
0901 ACCGTGGGGG CCACCACCTC CACCGACGCC AGGGCCTCCT ATTCCAACTA
0951 CGGTAGCTGC CTCGACCTCT TCGCCCCCGG CTCTTCCATC ACCTCGGCCT
1001 GGATTAGCAG CGACACCTCG ACCAACACCA TCAGCGGAAC CTCGATGGCC
1051 ACCCCCCATG TGGCCGGGGT AGCGGCTTTG TACCTGCAAA GCAACCCCAG
1101 TGCCAGCCCC GCCACCGTGC GCAACGCCAT TGTGGGCAAC GCCACTTCGG
1151 GTGTGGTGAG CAACGCCGGG CGGCGTTCGC CCAACCTGCT GCTGTACAGC
1201 AATTACTGA

FIG. 8B SEQ ID NO: 4

10 20 30 40 50 60
MYRLVWIALL LLLASCGNRA TPDNLAPVLG LDNPNVIQGQ YIVVYKDDAN VLPTLQSLKA 70 80 90 100 110 120
ALDGGVTLQR ELESLGLAPD ARVEQVYTAA LLGLAARLSP ENLAALRQDP RVAYIEADQV 130 140 150 160 170 180
MSISATQTGA TWGLDRIDQR TLPLSGTFTY SNTGSGVNAY IIDTGIRVSH SEFGGRATAV 190 200 210 220 230 240
FDAIGDGQNG NDCNGHGTHV AGTVGGTVYG VAKSVRLYAV RVLNCSGSGS NSGVIAGVDW 250 260 270 280 290 300
VRQNARRPAV ANMSLGGGAS SALDTAVNNA INAGITFALA AGNSNRDACQ FSPARVTAGI 310 320 330 340 350 360
TVGATTSTDA RASYSNYGSC LDLFAPGSSI TSAWISSDTS TNTISGTSMA TPHVAGVAAL 370 380 390 400
YLQSNPSASP ATVRNAIVGN ATSGVVSNAG RRSPNLLLYS NY

FIG. 9A

SEQ ID NO: 5

```
0001 ATGCTAGCCC CGGTGCTAGG ACTGGATAAC CCCAACGTTA TCCAGGGGCA
0051 GTACATTGTG GTCTACAAGG ATGATGCCAA CGTGCTGCCC ACCCTGCAAA
0101 GCCTGAAAGC CGCTTTAGAT GGGGGTGTAA CCCTTCAGCG GGAACTGGAA
0151 AGCCTGGGGC TGGCACCCGA CGCCAGGGTT GAGCAGGTTT ACACCGCTGC
0201 TCTGCTGGGG CTTGCGGCCC GGCTATCACC CGAGAATTTA GCCGCGCTGC
0251 GGCAGGATCC CCGGGTGGCC TACATCGAGG CCGACCAGGT CATGAGCATC
0301 AGCGCCACCC AGACCGGTGC GACCTGGGGC CTGGATCGCA TAGACCAGCG
0351 CACCCTACCC CTCAGCGGTA CCTTCACCTA CAGCAACACG GGCAGCGGCG
0401 TGAACGCCTA CATCATCGAT ACCGGTATCC GGGTGAGCCA CAGCGAGTTT
0451 GGCGGTCGGG CCACGGCGGT TTTCGACGCT ATTGGAGACG GCCAGAATGG
0501 CAACGACTGC AACGGCCATG GCACCCATGT GGCTGGAACG GTAGGCGGCA
0551 CGGTCTACGG CGTAGCCAAA AGCGTGCGGT TGTACGCGGT GCGGGTGCTT
0601 AATTGCAGCG GCTCGGGCAG CAACTCGGGC GTAATTGCCG GGGTGGACTG
0651 GGTGCGGCAG AATGCCCGGA GGCCAGCGGT AGCCAACATG AGCCTGGGTG
0701 GGGGGGCCTC GAGCGCCCTC GATACCGCGG TCAATAACGC CATCAACGCC
0751 GGGATTACCT TTGCCCTGGC CGCAGGTAAC AGCAACCGCG ACGCCTGCCA
0801 GTTCTCGCCA GCCCGCGTCA CTGCAGGCAT TACCGTGGGG GCCACCACCT
0851 CCACCGACGC CAGGGCCTCC TATTCCAACT ACGGTAGCTG CCTCGACCTC
0901 TTCGCCCCCG GCTCTTCCAT CACCTCGGCC TGGATTAGCA GCGACACCTC
0951 GACCAACACC ATCAGCGGAA CCTCGATGGC CACCCCCCAT GTGGCCGGGG
1001 TAGCGGCTTT GTACCTGCAA AGCAACCCCA GTGCCAGCCC CGCCACCGTG
1051 CGCAACGCCA TTGTGGGCAA CGCCACTTCG GGTGTGGTGA GCAACGCCGG
1101 GCGGCGTTCG CCCAACCTGC TGCTGTACAG CAATTACGAG AACCTCTACT
1151 TCCAATCGCA CCATCATCAC CACCATTGGA GCCATCCGCA GTTTGAAAAA
1201 TAG
```

FIG. 9B

SEQ ID NO: 6

```
        10         20         30         40         50         60
MLAPVLGLDN PNVIQGQYIV VYKDDANVLP TLQSLKAALD GGVTLQRELE SLGLAPDARV

        70         80         90        100        110        120
EQVYTAALLG LAARLSPENL AALRQDPRVA YIEADQVMSI SATQTGATWG LDRIDQRTLP

       130        140        150        160        170        180
LSGTFTYSNT GSGVNAYIID TGIRVSHSEF GGRATAVFDA IGDGQNGNDC NGHGTHVAGT

       190        200        210        220        230        240
VGGTVYGVAK SVRLYAVRVL NCSGSGSNSG VIAGVDWVRQ NARRPAVANM SLGGGASSAL

       250        260        270        280        290        300
DTAVNNAINA GITFALAAGN SNRDACQFSP ARVTAGITVG ATTSTDARAS YSNYGSCLDL

       310        320        330        340        350        360
FAPGSSITSA WISSDTSTNT ISGTSMATPH VAGVAALYLQ SNPSASPATV RNAIVGNATS

       370        380        390        400
GVVSNAGRRS PNLLLYSNYE NLYFQSHHHH HHWSHPQFEK
```

FIG. 10A-1 SEQ ID NO: 7 agatctaacatccaaagacgaaaggttgaatgaaacctttttgccatccgacatccacaggtccattctcacacataa
gtgccaaacgcaacaggaggggatacactagcagcagaccgttgcaaacgcaggacctccactcctcttctcctca
acacccacttttgccatcgaaaaaccagcccagttattgggcttgattggagctcgctcattccaattccttctattagg
ctactaacaccatgactttattagcctgtctatcctggcccccctggcgaggttcatgtttgtttatttccgaatgcaaca
agctccgcattacacccgaacatcactccagatgagggctttctgagtgtggggtcaaatagtttcatgttccccaaat
ggcccaaaactgacagtttaaacgctgtcttggaacctaatatgacaaaagcgtgatctcatccaagatgaactaag
tttggttcgttgaaatgctaacggccagttggtcaaaaagaaacttccaaaagtcggcataccgtttgtcttgtttggt
attgattgacgaatgctcaaaaataatctcattaatgcttagcgcagtctctctatcgcttctgaaccccggtgcacctg
tgccgaaacgcaaatggggaaacacccgctttttggatgattatgcattgtctccacattgtatgcttccaagattctg
gtgggaatactgctgatagcctaacgttcatgatcaaaatttaactgttctaacccctacttgacagcaatatataaac
agaaggaagctgccctgtcttaaaccttttttttatcatcattattagcttactttcataattgcgactggttccaattga
caagcttttgattttaacgacttttaacgacaacttgagaagatcaaaaaacaactaattattcgaaacg
ATGAGATTTCCTTCTATTTTTACTGCTGTTTTATTCGCAGCATCCTCCGCATTAGCTG
CTCCAGTCAACACTACAACAGAAGATGAAACGGCACAAATTCCGGCTGAAGCTGTCA
TCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAG
AAGAAGGGGTATCTCTCGAAAAAAGAGAGGCTGAAGC*AGAAGGAATTGGAGTGGCAG*
*GAATGCTAGCCCCGGTGCTAGGACTGGATAACCCCAACGTTATCCAGGGCAGTACAT*
*TGTGGTCTACAAGGATGATGCCAACGTGCTGCCCACCCTGCAAAGCCTGAAAGCCGCT*
*TTAGATGGGGGTGTAACCCTTCAGCGGGAACTGGAAAGCCTGGGGCTGGCACCCGAC*
*GCCAGGGTTGAGCAGGTTTACACCGCTGCTCTGCTGGGGCTTGCGGCCCGGCTATCAC*
*CCGAGAATTTAGCCGCGCTGCGGCAGGATCCCCGGGTGGCCTACATCGAGGCCGACCA*
*GGTCATGAGCATCAGCGCCACCCAGACCGGTGCGACCTGGGGCCTGGATCGCATAGAC*
*CAGCGCACCCTACCCCTCAGCGGTACCTTCACCTACAGCAACACGGGCAGCGGCGTGA*
*ACGCCTACATCATCGATACCGGTATCCGGGTGAGCCACAGCGAGTTTGGCGGTCGGGC*
*CACGGCGGTTTTCGACGCTATTGGAGACGGCCAGAATGGCAACGACTGCAACGGCCA*
*TGGCACCCATGTGGCTGGAACGGTAGGCGGCACGGTCTACGGCGTAGCCAAAAGCGT*
*GCGGTTGTACGCGGTGCGGGTGCTTAATTGCAGCGGCTCGGGCAGCAACTCGGGCGT*
*AATTGCCGGGGTGGACTGGGTGCGGCAGAATGCCCGGAGGCCAGCGGTAGCCAACAT*
*GAGCCTGGGTGGGGGGCCTCGAGCGCCCTCGATACCGCGGTCAATAACGCCATCAAC*
*GCCGGGATTACCTTTGCCCTGGCCGCAGGTAACAGCAACCGCGACGCCTGCCAGTTCT*
*CGCCAGCCCGCGTCACTGCAGGCATTACCGTGGGGGCCACCACCTCCACCGACGCCAG*
*GGCCTCCTATTCCAACTACGGTAGCTGCCTCGACCTCTTCGCCCCCGGCTCTTCCATCA*
*CCTCGGCCTGGATTAGCAGCGACACCTCGACCAACACCATCAGCGGAACCTCGATGGC*
*CACCCCCCATGTGGCCGGGGTAGCGGCTTTGTACCTGCAAAGCAACCCCAGTGCCAGC*
*CCCGCCACCGTGCGCAACGCCATTGTGGGCAACGCCACTTCGGGTGTGGTGAGCAACG*
*CCGGGCGGCGTTCGCCCAACCTGCTGCTGTACAGCAATTAC**GGGAACCTCTACTTCCAA*
*TCG*CATCATCATCATCATCATCACCATTGAgtttgtagccttagacatgactgttcctcagttcaag
ttgggcacttacgagaagaccggtcttgctagattctaatcaagaggatgtcagaatgccatttgcctgagagatgca
ggcttcatttttgatactttttatttgtaacctatatagtataggatttttttgtcattttgtttcttctcgtacgagcttgc
tcctgatcagcctatctcgcagctgatgaatatcttgtggtaggggtttgggaaaatcattcgagtttgatgtttttcttg
gtatttcccactcctcttcagagtacagaagattaagtgagaccttcgtttgtgcggatcccccacacaccatagcttc
aaaatgtttctactccttttttactcttccagattttctcggactccgcgcatcgccgtaccacttcaaaacacccaagca
cagcatactaaattttccctctttcttcctctagggtgtcgttaattacccgtactaaaggtttggaaaagaaaaaaga
gaccgcctcgtttctttttcttcgtcgaaaaaggcaataaaaatttttatcacgtttctttttcttgaaattttttttttagt FIG. 10A-2 SEQ ID NO: 7 (Continued)

tttttctctttcagtgacctccattgatatttaagttaataaacggtcttcaatttctcaagtttcagtttcatttttcttgtt
ctattacaactttttttacttcttgttcattagaaagaaagcatagcaatctaatctaaggggcggtgttgacaattaat
catcggcatagtatatcggcatagtataatacgacaaggtgaggaactaaaccatggccaagttgaccagtgccgtt
ccggtgctcaccgcgcgcgacgtcgccggagcggtcgagttctggaccgaccggctcgggttctcccgggacttcgt
ggaggacgacttcgccggtgtggtccgggacgacgtgaccctgttcatcagcgcggtccaggaccaggtggtgccg
gacaacaccctggcctgggtgtgggtgcgcggcctggacgagctgtacgccgagtggtcggaggtcgtgtccacga
acttccgggacgcctccgggccggccatgaccgagatcggcgagcagccgtgggggcgggagttcgccctgcgcg
acccggccggcaactgcgtgcacttcgtggccgaggagcaggactgacacgtccgacggcggcccacgggtccca
ggcctcggagatccgtcccccttttcctttgtcgatatcatgtaattagttatgtcacgcttacattcacgccctcccccc
acatccgctctaaccgaaaaggaaggagttagacaacctgaagtctaggtccctatttatttttttatagttatgttagt
attaagaacgttatttatatttcaaatttttcttttttttctgtacagacgcgtgtacgcatgtaacattatactgaaaacc
ttgcttgagaaggttttgggacgctcgaaggctttaatttgcaagctggagaccaacatgtgagcaaaaggccagca
aaaggccaggaaccgtaaaaaggccgcgttgctggcgtttttccataggctccgcccccctgacgagcatcacaaa
aatcgacgctcaagtcagaggtggcgaaacccgacaggactataaagataccaggcgtttccccctggaagctccc
tcgtgcgctctcctgttccgaccctgccgcttaccggatacctgtccgcctttctcccttcgggaagcgtggcgctttctc
aatgctcacgctgtaggtatctcagttcggtgtaggtcgttcgctccaagctgggctgtgtgcacgaaccccccgttca
gcccgaccgctgcgccttatccggtaactatcgtcttgagtccaacccggtaagacacgacttatcgccactggcagc
agccactggtaacaggattagcagagcgaggtatgtaggcggtgctacagagttcttgaagtggtggcctaactacg
gctacactagaaggacagtatttggtatctgcgctctgctgaagccagttaccttcggaaaaagagttggtagctctt
gatccggcaaacaaaccaccgctggtagcggtggtttttttgtttgcaagcagcagattacgcgcagaaaaaaagga
tctcaagaagatcctttgatcttttctacggggtctgacgctcagtggaacgaaaactcacgttaagggattttggtca
tgagatc

FIG. 10B SEQ ID NO: 8

MRFPSIFTAVLFAASSALAAPVNTTTEDETAQIPAEAVIGYSDLEGDFDVAVLPFSNSTNNGLLFI
NTTIASIAAKEEGVSLEKREAEAEGIGVAGM*LAPVLGLDNPNVIQGQYIVVYKDDANVLPTLQSL*
*KAALDGGVTLQRELESLGLAPDARVEQVYTAALLGLAARLSPENLAALRQDPRVAYIEADQVMSI*
*SATQTGATWGLDRIDQRTLPLSGTFTYSNTGSGVNAYIIDTGIRVSHSEFGGRATAVFDAIGD*
*GQNGNDCNGHGTHVAGTVGGTVYGVAKSVRLYAVRVLNCSGSGSNSGVIAGVDWVRQNA*
*RRPAVANMSLGGGASSALDTAVNNAINAGITFALAAGNSNRDACQFSPARVTAGITVGATT*
*STDARASYSNYGSCLDLFAPGSSITSAWISSDTSTNTISGTSMATPHVAGVAALYLQSNPSASP*
*ATVRNAIVGNATSGVVSNAGRRSPNLLLYSNY*GNLYFQSHHHHHHHH

FIG. 11A-1 SEQ ID NO: 9 agatctaacatccaaagacgaaaggttgaatgaaacctttttgccatccgacatccacaggtccattctcacacataa
gtgccaaacgcaacaggaggggatacactagcagcagaccgttgcaaacgcaggacctccactcctcttctcctca
acacccacttttgccatcgaaaaaccagcccagttattgggcttgattggagctcgctcattccaattccttctattagg
ctactaacaccatgactttattagcctgtctatcctggcccccctggcgaggttcatgtttgtttatttccgaatgcaaca
agctccgcattacacccgaacatcactccagatgagggctttctgagtgtggggtcaaatagtttcatgttccccaaat
ggcccaaaactgacagtttaaacgctgtcttggaacctaatatgacaaaagcgtgatctcatccaagatgaactaag
tttggttcgttgaaatgctaacggccagttggtcaaaaagaaacttccaaaagtcggcataccgtttgtcttgtttggt
attgattgacgaatgctcaaaaataatctcattaatgcttagcgcagtctctctatcgcttctgaaccccggtgcacctg
tgccgaaacgcaaatggggaaacacccgctttttggatgattatgcattgtctccacattgtatgcttccaagattctg
gtgggaatactgctgatagcctaacgttcatgatcaaaatttaactgttctaacccctacttgacagcaatatataaac
agaaggaagctgccctgtcttaaaccttttttttatcatcattattagcttactttcataattgcgactggttccaattga
caagcttttgattttaacgacttttaacgacaacttgagaagatcaaaaaacaactaattattcgaaacg
ATGAGATTTCCTTCTATTTTTACTGCTGTTTTATTCGCAGCATCCTCCGCATTAGCTG
CTCCAGTCAACACTACAACAGAAGATGAAACGGCACAAATTCCGGCTGAAGCTGTCA
TCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAG
AAGAAGGGGTATCTCTCGAAAAAAGAGAGGCTGAAGC*AGAAGGAATTGGAGTGGCAG*
*GA* *GCCACCCAGACCGGTGCGACCTGGGGCCTGGATCGCATAGACCAGCGCACCCTACC*
*CCTCAGCGGTACCTTCACCTACAGCAACACGGGCAGCGGCGTGAACGCCTACATCATC*
*GATACCGGTATCCGGGTGAGCCACAGCGAGTTTGGCGGTCGGGCCACGGCGGTTTTC*
*GACGCTATTGGAGACGGCCAGAATGGCAACGACTGCAACGGCCATGGCACCCATGTG*
*GCTGGAACGGTAGGCGGCACGGTCTACGGCGTAGCCAAAAGCGTGCGGTTGTACGCG*
*GTGCGGGTGCTTAATTGCAGCGGCTCGGGCAGCAACTCGGGCGTAATTGCCGGGGTG*
*GACTGGGTGCGGCAGAATGCCCGGAGGCCAGCGGTAGCCAACATGAGCCTGGGTGGG*
*GGGGCCTCGAGCGCCCTCGATACCGCGGTCAATAACGCCATCAACGCCGGGATTACCT*
*TTGCCCTGGCCGCAGGTAACAGCAACCGCGACGCCTGCCAGTTCTCGCCAGCCCGCGT*
*CACTGCAGGCATTACCGTGGGGGCCACCACCTCCACCGACGCCAGGGCCTCCTATTCC*
*AACTACGGTAGCTGCCTCGACCTCTTCGCCCCCGGCTCTTCCATCACCTCGGCCTGGAT*
*TAGCAGCGACACCTCGACCAACACCATCAGCGGAACCTCGATGGCCACCCCCCATGTG*
*GCCGGGGTAGCGGCTTTGTACCTGCAAAGCAACCCCAGTGCCAGCCCCGCCACCGTGC*
*GCAACGCCATTGTGGGCAACGCCACTTCGGGTGTGGTGAGCAACGCCGGGCGGCGTTC*
*GCCCAACCTGCTGCTGTACAGCAATTAC* *GGAACCTCTACTTCCAATCG* CATCATCAT
CATCATCATCACCATTGA
gtttgtagccttagacatgactgttcctcagttcaagttgggcacttacgagaagaccggtcttgctagattctaatca
agaggatgtcagaatgccatttgcctgagagatgcaggcttcatttttgatactttttatttgtaacctatatagtatag
gatttttttgtcattttgtttcttctcgtacgagcttgctcctgatcagcctatctcgcagctgatgaatatcttgtggtag
gggtttgggaaaatcattcgagtttgatgtttttcttggtatttcccactcctcttcagagtacagaagattaagtgaga
ccttcgtttgtgcggatcccccacacaccatagcttcaaaatgtttctactccttttttactcttccagattttctcggact
ccgcgcatcgccgtaccacttcaaaacacccaagcacagcatactaaattttccctctttcttcctctagggtgtcgtta
attacccgtactaaaggtttggaaaagaaaaaagagaccgcctcgtttctttttcttcgtcgaaaaaggcaataaaaa
tttttatcacgtttctttttcttgaaatttttttttttagtttttttctctttcagtgacctccattgatatttaagttaataaac
ggtcttcaatttctcaagtttcagtttcatttttcttgttctattacaactttttttacttcttgttcattagaaagaaagcat
agcaatctaatctaaggggcggtgttgacaattaatcatcggcatagtatatcggcatagtataatacgacaaggtg
aggaactaaaccatggccaagttgaccagtgccgttccggtgctcaccgcgcgcgacgtcgccggagcggtcgagt
tctggaccgaccggctcgggttctcccgggacttcgtggaggacgacttcgccggtgtggtccgggacgacgtgacc
ctgttcatcagcgcggtccaggaccaggtggtgccggacaacaccctggcctgggtgtgggtgcgcggcctggacg FIG. 11A-2 SEQ ID NO: 9 (Continued)

agctgtacgccgagtggtcggaggtcgtgtccacgaacttccgggacgcctccgggccggccatgaccgagatcgg
cgagcagccgtgggggcgggagttcgccctgcgcgacccggccggcaactgcgtgcacttcgtggccgaggagca
ggactgacacgtccgacggcggcccacgggtcccaggcctcggagatccgtcccccttttcctttgtcgatatcatgt
aattagttatgtcacgcttacattcacgccctccccccacatccgctctaaccgaaaaggaaggagttagacaacctg
aagtctaggtccctatttatttttttatagttatgttagtattaagaacgttatttatatttcaaatttttcttttttttctgtac
agacgcgtgtacgcatgtaacattatactgaaaaccttgcttgagaaggttttgggacgctcgaaggctttaatttgca
agctggagaccaacatgtgagcaaaaggccagcaaaaggccaggaaccgtaaaaaggccgcgttgctggcgtttt
tccataggctccgcccccctgacgagcatcacaaaaatcgacgctcaagtcagaggtggcgaaacccgacaggact
ataaagataccaggcgtttccccctggaagctccctcgtgcgctctcctgttccgaccctgccgcttaccggatacctg
tccgcctttctcccttcgggaagcgtggcgctttctcaatgctcacgctgtaggtatctcagttcggtgtaggtcgttcg
ctccaagctgggctgtgtgcacgaaccccccgttcagcccgaccgctgcgccttatccggtaactatcgtcttgagtcc
aacccggtaagacacgacttatcgccactggcagcagccactggtaacaggattagcagagcgaggtatgtaggcg
gtgctacagagttcttgaagtggtggcctaactacggctacactagaaggacagtatttggtatctgcgctctgctga
agccagttaccttcggaaaaagagttggtagctcttgatccggcaaacaaaccaccgctggtagcggtggtttttttg
tttgcaagcagcagattacgcgcagaaaaaaaggatctcaagaagatcctttgatcttttctacggggtctgacgctc
agtggaacgaaaactcacgttaagggattttggtcatgagatc

FIG. 11B SEQ ID NO: 10

MRFPSIFTAVLFAASSALAAPVNTTTEDETAQIPAEAVIGYSDLEGDFDVAVLPFSNST
NNGLLFINTTIASIAAKEEGVSLEKREAEAEGIGVAG*ATQTGATWGLDRIDQRTLPLSG*
*TFTYSNTGSGVNAYIIDTGIRVSHSEFGGRATAVFDAIGDGQNGNDCNGHGTHVAGTV*
*GGTVYGVAKSVRLYAVRVLNCSGSGSNSGVIAGVDWVRQNARRPAVANMSLGGGASS*
*ALDTAVNNAINAGITFALAAGNSNRDACQFSPARVTAGITVGATTSTDARASYSNYGS*
*CLDLFAPGSSITSAWISSDTSTNTISGTSMATPHVAGVAALYLQSNPSASPATVRNAIV*
*GNATSGVVSNAGRRSPNLLLYSNY*GNLYFQSHHHHHHHH

HEAT STABLE KERATINASE AND USE THEREOF

REFERENCE TO RELATED APPLICATION

This application is a national stage application (under 35 U.S.C. 371) of PCT/US2014/047052 filed on 17 Jul. 2014, which claims priority to U.S. provisional application 61/859,720 filed on 29 Jul. 2013, all of which are herein incorporated by reference in their entireties.

FIELD OF THE INVENTION

The present invention relates to proteases, and more specifically to microbial keratinases isolated from *Meiothermus Taiwanesis.*

BACKGROUND OF THE INVENTION

Keratins, a family of fibrous structure proteins, are the key structural components of skin, hair, wools, nails, scales and feathers. Keratin polypeptides are insoluble and resistant to most proteases. Accumulation of insoluble keratins in the environment, mainly in the form of feathers and hair, becomes an issue in the solid waste management.

Keratins can be efficiently degraded by keratinases. Hence, keratinases find applications in biowaste process and also in detergent and leather industries where they serve as specialty enzymes to remove proteinaceous stains and hair, respectively. The applications can also be extended to wool and silk cleaning and medicine. Recently, keratinase has been used extensively to increase digestibility of proteins in animal feed.

Heat is often required in industrial applications to speed up reactions. The spray drying process of keratinase powder also requires heating. Hence, a heat-stable keratinase can be very useful in the industries.

SUMMARY OF THE INVENTION

In one aspect, the invention relates to a fusion gene comprising: (a) a first DNA sequence encoding a protein secretion signal peptide, located at the N-terminus of the fusion gene; (b) a second DNA sequence encoding an inhibitory domain of *M. taiwanensis* WR-220 keratinase, linked in translation frame with the first DNA sequence; and (c) a third DNA sequence encoding a catalytic domain of *M. taiwanensis* WR-220 keratinase, linked in translation frame with the second DNA sequence, wherein the fusion gene is a non-naturally occurring chimeric DNA.

The protein secretion signal peptides may be selected from the group consisting of alpha-amylase signal peptide, glucoamylase signal peptide, serum albumin signal peptide, inulinase signal peptide, invertase signal peptide, killer virus signal peptide, Lysozyme signal peptide, mating factor alpha-1 signal peptide, and mating factor alpha-2 signal peptide.

In one embodiment of the invention, the first DNA sequence encodes a yeast alpha-factor signal peptide.

In another aspect, the invention relates to a protein expression vector comprising: (a) the fusion gene as aforementioned; and (b) a promoter, linked in translation frame with the fusion gene. The promoter may be selected from the group consisting of alcohol oxidase (AOX) promoter, glyceraldehyde phosphate dehydrogenase promoter, translational elongation factor 1-α promoter, $Na^+$-coupled phosphate symproter promoter, and formaldehyde dehydrogenase promoter.

In another aspect, the invention relates to a host cell comprising the expression vector as aforementioned.

In another aspect, the invention relates to a cell culture comprising the host cell as aforementioned and an artificial medium, the host cell secreting the catalytic domain of *M. taiwanensis* WR-220 keratinase into the artificial medium.

In another embodiment of the invention, the second DNA sequence comprises a nucleotide sequence having at least 90% or 95% identity to SEQ ID NO: 11.

In another aspect, the invention relates to an isolated protease comprising a catalytic domain of *M. taiwanensis* WR-220 keratinase, the protease lacking an inhibitory domain of *M. taiwanensis* WR-220 keratinase, and being in the form of a tablet, a caplet, a pellet, a capsule, a granule, a pill, a powder or a sachet, or in the form of a solution without containing a cell culture supplement. In one embodiment of the invention, The protease comprises an amino acid sequence having at least 95% identity to SEQ ID NO: 14.

Further in another aspect, the invention relates to a method for degrading a proteinaceous material, comprising: exposing the proteinaceous material to an effective amount of the protease as aforementioned. Prior to the exposing step, the method may further comprise the step of preparation of the catalytic domain of *M. taiwanensis* WR-220 keratinase.

Alternative, the invention relates to use of the fusion gene for preparation of a protease as aforementioned for degrading a proteinaceous material.

The invention further relates to use of the fusion gene as aforementioned in the manufacture of a protease for degrading a proteinaceous material. Alternatively, the invention relates to use of a protease as aforementioned in manufacture of a composition for degrading a proteinaceous material. The use may be performed at a temperature above 25° C. Prior to the use, the protease may be pretreated at a temperature above 40° C. but below 95° C., or pretreated with a solution having a pH value ranging from 3 to 10, and still remains its activity. The proteinaceous material may be selected from the group consisting of animal feed, food, milk, casein, elastin, skin, hair, wool, silk, nails, scales, fiber, leather, and feathers.

Further in another aspect, the invention relates to a method for preparation of the catalytic domain of *M. taiwanensis* WR-220 keratinase, comprising: (ai) growing the host cell as aforementioned in a culture medium under conditions that permits expression of *M. taiwanensis* WR-220 keratinase and secretion of the catalytic domain thereof into the medium; or (aii) growing a host cell transformed with an expression plasmid comprising a DNA insert encoding an inhibitory domain and a catalytic domain of *M. taiwanensis* WR-220 keratinase under conditions that permits expression of *M. taiwanensis* WR-220 keratinase and secretion of the catalytic domain thereof into the medium; and (b) removing the host cell to obtain a supernatant containing the catalytic domain of the *M. taiwanensis* WR-220 keratinase; and (c) isolating the catalytic domain from the supernatant or removing liquid from the supernatant by a spray drying method or others to obtain the catalytic domain in a solid form.

Yet in another aspect, the invention relates to an isolated protease comprising a catalytic domain and lacking an inhibitory domain of *M. taiwanensis* WR-220 keratinase, the protease being prepared from the method as aforementioned.

In another embodiment of the invention, the inhibitory domain comprises an amino acid sequence having at least 95% identity to SEQ ID NO: 13; and the catalytic domain comprises an amino acid sequence having at least 95% identity to SEQ ID NO: 14. Alternatively, the inhibitory domain comprises an amino acid sequence of SEQ ID NO: 13; and the catalytic domain comprises an amino acid sequence of SEQ ID NO: 14.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 8A shows the nucleotide sequence of the SPR2261 gene (SEQ ID NO: 3). The part cloned is shown in bold. The predicted signal peptide for protein secretion is shown in italic.

FIG. 8B shows the amino acid sequence of SPR2261 (SEQ ID NO: 4). The predicted signal peptide for protein secretion is labeled in italic, the predicted inhibitory domain labeled as underlined, and the active form of keratinase labeled in bold only.

FIG. 9A shows the cloned DNA sequence of keratinase (SEQ ID NO: 5). The first methionine (starting codon) is labeled as underlined, the inhibitory domain labeled in non-bold, the active form of truncated keratinase labeled in bold only, and a fusion tag for purification labeled in italic.

FIG. 9B shows the amino acid sequence of cloned keratinase (SEQ ID NO: 6) from *Meiothermus taiwanensis* WR-220. The first methionine (starting codon) is labeled as underline, the inhibitory domain labeled in non-bold, the active form of truncated keratinase labeled in bold only, and a fusion tag for protein purification labeled in italic.

FIGS. 10A-B show the nucleotide sequence of the plasmid construct pHTPY2_spr2261ic (SEQ ID NO: 7) and its corresponding keratinase protein sequence (SEQ ID NO: 8). (A-1, A-2) The genes of alpha factor is labeled as underline, LIC cloning sites labeled in italic, inserted spr2261ic (containing inhibitory and catalytic domains) labeled in bold with italic, and 8×His tag with a stop codon labeled in bold only. (B) The corresponding expressed protein sequence (SEQ ID NO: 8) comprises the alpha factor (SEQ ID NO: 15) labeled as underline, the inhibitory domain labeled in italic only, and catalytic domain labeled in bold with italic, and 8×His tag labeled in bold only.

FIGS. 11A-B show the nucleotide sequence of the plasmid construct of pHTPY2_spr2261c (SEQ ID NO: 9) and its corresponding keratinase protein sequence (SEQ ID NO: 10). (A-1, A-2) The alpha factor labeled as underline, LIC cloning sites labeled in italic, inserted spr2261c (containing only the catalytic domain but without the inhibitory domain) labeled in bold with italic, and 8×His tag (with a stop codon) labeled in bold. (B) The corresponding expressed protein sequence comprises the alpha factor labeled as underline, the catalytic domain labeled in bold with italic, and 8×His tag labeled in bold only, but does not comprise the inhibitory domain.

DETAILED DESCRIPTION OF THE INVENTION

Definitions

Figure 1A:
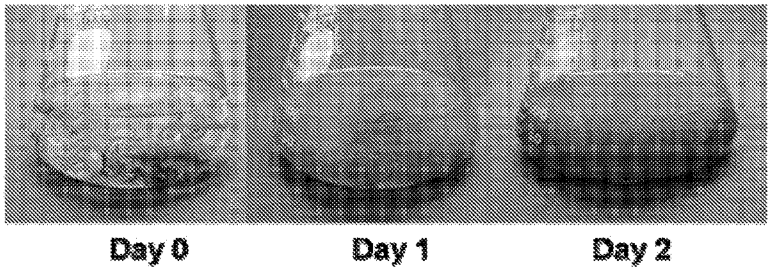
FIGS. 1A-C show degradation ability of intact chicken feathers by *M. taiwanensis* WR-220. (A) The culture medium containing feathers as carbon and nitrogen sources is clear at Day 0. The cloudy medium at Day 2 indicates the degradation of feathers and the growth of microbes. (B) Photographs showing the remaining feathers in the medium. (C) Graphs showing the weight of the remaining feathers (left panel) or insoluble residues in the culture medium and the amount of soluble free-amino acid (right panel) from decayed feathers in the culture supernatant with or without the presence of *M. taiwanensis*.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Protein secretion signal peptides determines the efficiency of protein secretion. They include, but not limited to, alpha-amylase signal peptide (SEQ ID NOs: 17, 18), glucoamylase signal peptide (SEQ ID NOs: 19, 20), serum albumin signal peptide (SEQ ID NOs: 21, 22), inulinase signal peptide (SEQ ID NOs: 23, 24), invertase signal peptide (SEQ ID NOs: 25, 26), killer virus signal peptide (SEQ ID NOs: 27, 28), Lysozyme signal peptide (SEQ ID NOs: 29, 30), mating factor alpha-1 signal peptide (SEQ ID NOs: 31, 32), and mating factor alpha-2 signal peptide (SEQ ID NOs: 33, 34).

As used herein, "an inhibitory domain of *M. taiwanensis* WR-220 keratinase" refers to an amino acid sequence having at least 90% identity to SEQ ID NO: 13. Thus, as used herein "an inhibitory domain of *M. taiwanensis* WR-220 keratinase" includes a wild-type or a mutant inhibitory domain of *M. taiwanensis* WR-220 keratinase, wherein the mutant inhibitory domain comprises an amino acid sequence having at least 90% identity to SEQ ID NO: 13.

As used herein, "a catalytic domain of *M. taiwanensis* WR-220 keratinase" refers to a protease that comprises an amino acid sequence having at least 90% identity to SEQ ID NO: 14. Thus, as used herein "a catalytic domain of *M. taiwanensis* WR-220 keratinase" includes a wild-type or a mutant catalytic domain of *M. taiwanensis* WR-220 keratinase, wherein the mutant catalytic domain comprises an amino acid sequence having at least 90% identity to SEQ ID NO: 14.

*M. taiwanensis* WR-220, a thermophilic species found in Taiwan, habits in the temperature ranging from 55 to 65° C. The proteins produced in *M. taiwanensis* must remain stable at temperature over 55° C., an ability that renders the proteins suitable for industrial use.

The invention relates to the discovery of *M. taiwanensis* keratinase that not only possesses a high stability against heat, acidic and basic environment but also exhibits a wide range proteolytic activity. The heat and acid tolerance is useful for industrial applications.

The invention further relates to an expression plasmid for the production of recombinant *M. taiwanensis* WR-220 keratinase as secreted protein using methylotrophic *Pichia pastori* expression systems, which is under the control of the promoter of alcohol oxidase gene. *P. pastoris* itself does not secrete any endogenous keratinase into the cultivation medium. In addition, *P. pastoris* is generally regarded as safe (GRAS) and has an added advantage for recombinant keratinase production.

It was discovered that *M. taiwanensis* WR-220 was able to degrade feathers. The corresponding keratinase was then isolated and its DNA and amino acid sequences were identified. The keratinase with a fusion tag was cloned to the vector for recombinant protein production using *E. coli* expression system. The recombinant and truncated keratinase showed a wide range protease activity that could hydrolyze proteins in skim milk, casein, elastin and feathers. Moreover, the recombinant keratinase not only possessed a high stability against heat, acidic and basic environment but also exhibited a wide range of proteolytic activity, which may be useful for industrial applications.

Inhibitory domain DNA sequence: SEQ ID NO: 11; Catalytic domain DNA sequence: SEQ ID NO: 12. Inhibitory domain protein sequence: SEQ ID NO: 13; Catalytic domain protein sequence: SEQ ID NO: 14.

Examples

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods and Materials

Cell Culture and Feather Degradation Assay.

*M. taiwanensis* WR-220, a gift from Dr. San-San Tsay, was incubated in a modified *Thermus* medium (TM medium) at 55° C. The modified TM medium contained 0.3% of peptone, 0.1% of yeast extract, 0.1% of glutamic acid, and 1× Castenholtz salts (pH 7.8). For the feather degradation, 1% of the overnight culture was added to the medium supplemented with 3% (w/v) intact chicken feathers and 1× Castenholtz salts at 55° C. and 65° C. The change in the weight of remaining feathers in the culture was examined by weighting the insoluble residues along the cultivation. The insoluble residues were obtained and weighted after the filtration of the culture using filter papers. The amount of the released amino acids from decayed feathers was quantified by the ninhydrin colorimetric method (Rosen, H. A "Modified ninhydrin colorimetric analysis for amino acids" Arch Biochem Biophys (1957) 67, 10-15).

Isolation of Keratinase from *M. taiwanensis* WR-220.

*M. taiwanensis* was cultured in 4 liters of TM medium. The cultivated medium was centrifuged at 6,000×g for 20 minutes and the supernatant was filtered with a 0.22 μm filter to remove microbes and insoluble residues. The collected supernatant was concentrated and buffer exchanged to 50 mL PBS buffer (pH 7.4) using a LABSCALE™ TFF system (Millipore, USA). The pigments were removed by ultracentrifugation at 137.24×g and the supernatant was further concentrated to 2 mL using Amicon-Ultra 15 centrifugal filter devices. The concentrated sample was loaded into a 1-mL resource S column (GE Healthcare, USA) pre-equilibrated with 50 mM sodium acetate buffer (pH 5.0). The protein was eluted with a linear gradient of NaCl from 0 to 1 M in 50 mM sodium acetate buffer (pH 5.0). Each fraction was collected and examined for feather degradation ability using zymography assay.

Zymography Assay and Identification of Amino Acid Sequence of Keratinase.

Proteins in each chromatographic fraction were further separated by 4 to 20% SDS-PAGE using Laemmli method (Laemmli, U. K. "*Cleavage of structural proteins during the assembly of the head of bacteriophage T4*" *Nature* (1970) 227, 680-685). The SDS-PAGE was washed with a 1.5% Triton X-100 solution twice, which allowed the target extracellular proteases in SDS-PAGE to retain their activities for further zymography assay. The renatured gel was then put on 1% agarose with keratin/casein powder in PBS buffer. Areas of proteolytic activities appeared as clear zones of lysis in the stained agarose replica. The proteins in the areas of proteolytic activities were identified by a standard proteomic analysis using *M. taiwanensis* genomic sequence as the reference (our unpublished result, NCBI bioproject submission ID: SUB251796 and bioproject ID: PRJNA205607). The proteomics analyses indicated that the annotated SPR2261 was most likely to be keratinase.

Molecular Cloning of Keratinase Gene to Protein Expression Vector.

The chromosomal DNA extracted using standard phenol extraction method was used to amplify keratinase gene using phusion flash high-fidelity PCR master mix (Thermo Scientific, USA) with forward

```
(5'TTA AGA AGG AGA TAT ACC

ATG CTA GCC CCG GTG CTA GGA; SEQ ID NO: 1)
```

and reverse

```
(5'GAT TGG AAG TAG AGG TTC TCT GC G

TAA TTG CTG TAC AGC AGC AGG TTG; SEQ ID NO: 2)
```

primers. The sites for cloning purpose are underlined. The PCR products were purified by electrophoresis and treated with T4 DNA polymerase in the presence of dGTP. The modified pET9 vector that contained the corresponding ligation independent cloning site, TEV protease site, and two affinity tags (6×His and Strep) was amplified by phusion flash high-fidelity PCR master mix, followed by dpnI treatment (Thermo Scientific, USA) and purified by PCR clean up kit (Geneaid, Taiwan). The linearized vector was then treated with T4 DNA polymerase (Thermo Scientific, USA) in the presence of dCTP. The keratinase gene and the vector were annealed and transformed into *E. coli* DH5α. The plasmid encoding keratinase extracted from successful clones was sent for DNA sequence analysis and the translated protein sequence was listed in FIG. 8B (SEQ ID NO: 4).

Enzyme Purification and Preparation.

The plasmid containing keratinase was transformed into *E. coli* (DE3) ArticExpress cell and grown overnight at 37° C. in 20 mL of TB medium containing 50 μg/mL of kanamycin and 10 μg/mL of tetracycline. The cultures were transferred into 1 L of TB containing the antibiotics, 5% lactose and 0.5% glucose at 37° C. for 4 h and then were cooled to 20° C. for overnight expression. The cells were harvested by centrifugation at 6000×g for 30 min and resuspended by lysis buffer (20 mM imidazole, 250 mM NaCl, and 50 mM HEPES, pH 8.0) in the presence of DNase I (5 μg/mL) and lysozyme (1 mg/mL) on ice for 30 min. The cells were disrupted by sonication, followed by centrifugation at 20000×g for 30 min. The supernatant was loaded onto a 2 mL Ni Sepharose (GE healthcare) column that was pre-equilibrated with 20 mL lysis buffer. The column was washed by 25 mL wash buffer (50 mM imidazole, 250 mM NaCl, and 50 mM HEPES, pH 8.0). The keratinase was eluted with 10 mL elution buffer (250 mM imidazole, 250 mM NaCl, and 50 mM HEPES, pH 8.0). The eluted keratinase was dialyzed against the solution containing 10 mM $CaCl_2$, 150 mM NaCl and 50 mM HEPES, pH8.0 and concentrated to ~10 mg/mL. The molecular weight of recombinant keratinase was determined by protein electrophoresis and MS spectrometry.

Crystallization, Data Collection and Structure Determination.

The keratinase was crystallized in 0.2M lithium sulfate, 0. IM sodium acetate and 50% PEG400 at 19° C. using a sitting drop vapor diffusion method. Crystals were flash-cooled in liquid nitrogen prior to data collection. X-ray diffraction data were collected at 15A beamline of National Synchrotron Radiation Resource Center on an ADSC Q315 detector at 100K. Data were processed using HKL2000 program suite. The structure of the keratinase was determined by molecular replacement using the crystal structure of Aqualysin I (PDB ID: 4DZT). Models were iteratively rebuilt in COOT and refined in Refmac5.

Paper Disk-Agar Diffusion Assay for Keratinase and Protease Activity.

Protease or keratinase activities were measured by 1% agarose supplemented with 1% skim milk, 1% casein, 1% elastin, or 1% feather powder in 150 mM $NaCl_2$, 10 mM $CaCl_2$ and 50 mM CHES buffer at pH8.6. Disc-shaped filter papers soaked with keratinase were lightly pressed onto the agar surface at 55° C. A clear zone around each disc indicated protease or keratinase activities.

The Heat and pH Tolerance Tests.

For the heat tolerance test, keratinase solutions (1.6 mg/mL in the solution containing 10 mM $CaCl_2$, 150 mM NaCl and 50 mM HEPES at pH8.0) were heated to corresponding temperatures for 2 mins. For the pH tolerance test, keratinase solutions (1.6 mg/mL) were prepared in the solutions containing 10 mM $CaCl_2$ and 100 mM corresponding buffers (phosphate, pH 2.0; citric acid, pH 3.0; citric acid, pH 4.0; phosphate, pH 5.0; phosphate, pH 6.0; phosphate, pH7.0; HEPES, pH 8.0; TAPS, pH 8.0; borate, pH 9.0; CAPS, pH 10.0; CAPS, pH 11.0). The remaining protease activities were examined by a paper disk-agar diffusion assay using a 5% skim milk agar plate.

Construct of the Recombinant Plasmids.

The pHTPY2 vector was modified by removing its cloning, TEV and part of 6× His tag sites and incorporating the designed ligation independent site, TEV and 8×His tag sites right after the alpha factor signal sequence, Kex2 signal cleavage and Ste13 signal cleavage sites (Wang et al. "Parallel Gene Cloning and Protein Production in Multiple Expression Systems" *Biotechnol Progr* (2009) 25, 1582-1586). Two different recombinant *M. taiwanensis* WR-220 keratinase gene constructs were amplified by PCR and ligated with the modified pHTYP2. One, pHTPY2_spr2261ic, contained the inhibitory domain and the catalytic domain (FIGS. 10A-B) and the other, pHTPY2_spr2261c, only contained the catalytic domain (FIG. 11A-B). The recombinant plasmids, pHTPY2 spr2261ic and pHTPY2_spr2261c were transformed into *E. coli* DH5α on low salt LB agar plates with 25 μg/ml zeocin. The positive clones were identified by colony PCR and the sequences were confirmed by DNA sequencing.

Transformation.

About 35 μg plasmids were linearized using pmeI and purified by alcohol precipitation prior to transformation into *P. pastoris* X33 strain by electroporation. The positive colonies were chosen from YPDS plates with 100 μg/ml zeocin at 30° C. and validated by the MD/MM plate method.

Small Scale Keratinase Production.

The positive colonies were cultivated in 5 ml of YPD medium with 100 μg/ml zecoin at 29° C. under agitation at 300 rpm in dark. The cells were collected by centrifugation until OD600 of 2-6 was reached and diluted to BMM medium (1.34% YNB, 4 E-5% biotin, 0.5% methanol and 100 mM potassium phosphate, pH 5.0) with 100 μg/ml ampicillin until OD600 value was reached to 2. Cells were cultured at 30° C. under agitation at 300 rpm. After one day incubation, the culture medium was supplemented with methanol to a final concentration of 0.5% every day. The culture supernatant was collected every 24 hour until day 5 and stored at 4° C.

SDS-PAGE and Mass Spectrometry Analyses.

The proteins in 480 μl of the culture supernatant were precipitated by addition of 120 μl of 100% TCA for 10 mins on ice, followed by centrifugation. The pellets were washed by 200 μl of cold acetone for three time and incubated at 95° C. for 5-10 mins to remove remaining acetone prior to the SDS-PAGE electrophoresis. The bands observed in the SDS-PAGE was treated by in-gel tryptic digestion prior to Mass spectrometric characterization.

Paper Disk-Agar Diffusion Assay for Protease Activity after Heat/pH Pretreatment.

Protease activities were detected by 1% agarose supplemented with 1% skim milk powder in 150 mM $NaCl_2$, 10 mM $CaCl_2$ and 50 mM HEPES buffer at pH8.0. Disc-shaped filter papers soaked with culture supernatant were lightly pressed onto the agar surface at 55° C. A clear zone around each disc indicated protease or keratinase activities.

Results

Keratinase Ability of *Meiothermus taiwanensis* WR-220

Figure 1B:
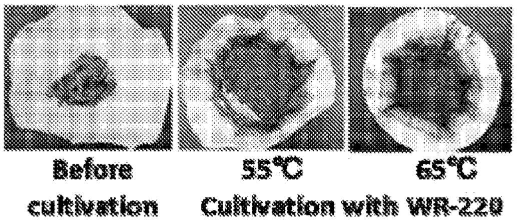
Figure 1C:
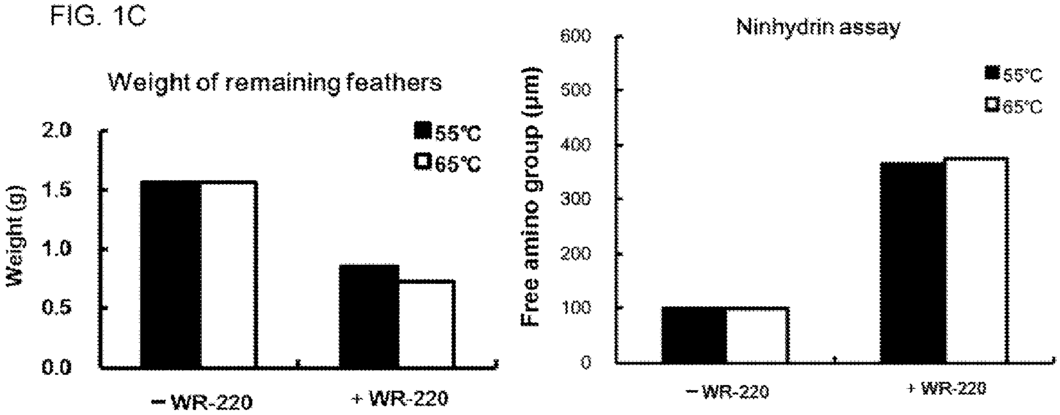

*M. taiwanensis* WR-220 was incubated in the medium with insoluble feathers as the only source of nutrients. The cloudy medium and reduction of feathers indicated that degradation occurred (FIG. 1A), suggesting *M. taiwanensis* could produce enzymes to consume feathers (FIG. 1). It was further found that *M. taiwanensis* WR-220 was able to degrade half of 3% feathers and release free amino acids from feathers in 2 days at 55° C. and 65° C. (FIGS. 1A-C).

Isolation and Identification Keratinase

Figure 2A:
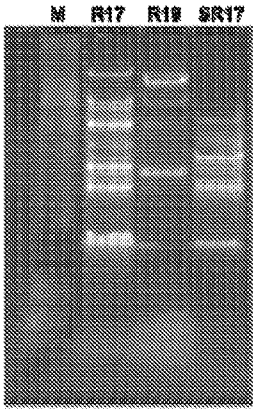
FIGS. 2A-B are photographs showing protein electrophoresis for the fractions of extracellular proteases secreted by *M. taiwanensis* WR-220, and an zymography assay where areas of keratinase activity appear as clear zones of the stained agarose replica, respectively. (A) 4-20% gradient SDS-PAGE stained by SYPRORUBY™. (B) 1% agarose within keratin/casein powders.
Figure 2B:
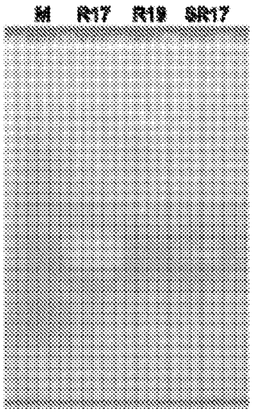

*M. taiwanensis* was removed from the growth medium and it was further found that the keratinase activity was kept in the medium, suggesting keratinase was produced as a secreted form. The total proteins were fractionated from the medium using ion exchange chromatography. The fractionated proteins were further separated by protein electrophoresis, following by zymography assay (FIGS. 2A-B). The zymography assay clearly showed that proteins in multiple areas of gel could digest keratin/casein. We then applied proteomics methods to identify the proteins in those areas using our genomic sequencing result (NCBI bioproject submission ID: SUB251796) as the reference. The translated amino acid sequence consisted of a predicted signal peptide, the predicated inhibitory domain and the predicated catalytic domain as shown in FIG. 8B (SEQ ID NO: 4). The cross comparison indicated that the gene SPR2261 is the putative keratinase of *M. taiwanensis* WR-220 (FIG. 8A; SEQ ID NO: 3), however, the sequence of the catalytic core shares only 39% sequence identity to the known keratinase from *Bacillus lifeniformis.*

Production of Recombinant Keratinase by *E. coli* Expression System

Figure 3:
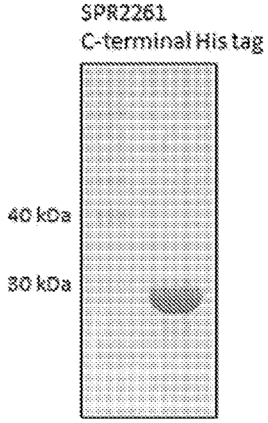
FIG. 3 is a photograph of protein electrophoresis, indicating the molecular weight of the recombinant keratinase is less than 30 KDa.

The keratinase gene (SPR2261) was amplified by PCR and cloned into an expression plasmid containing a starting codon and a fusion tag for *E. coli* expression system (FIG. 9A, SEQ ID NO: 5). The recombinant keratinase with an expected molecular weight of ~41.5 KDa was expressed in *E. coli* BL21 (DE3) Arctic cells and purified by affinity chromatography. The results of protein electrophoresis indicated that the molecular weight of the purified protein was ~28.5 kDa, suggesting a truncated form of cloned keratinase (FIG. 3), which was consistent with the 28,468 Dalton found by ESI-MS spectrometry. Our further structural analysis of keratinase by protein crystallography showed that the truncated form of the recombinant keratinase started from 102th residue of the cloned amino acid sequence (FIG. 9B, SEQ ID NO: 6).

Broad Protease Activity of Recombinant Keratinase and Heat pH Pretreatment

Figure 4:
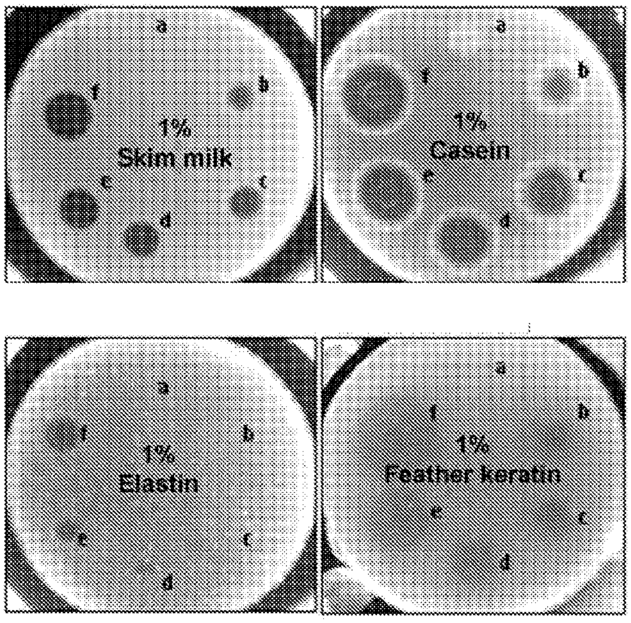
FIG. 4 is a series of photographs showing that the recombinant keratinase exhibits a broad range of proteolytic activities against proteins in milk, casein, elastin and feathers. The 0 μg, 1 μg, 2 μg, 4 μg, 8 μg and 16 μg of keratinases are labeled as a, b, c, d, and e, respectively.
Figure 5A:
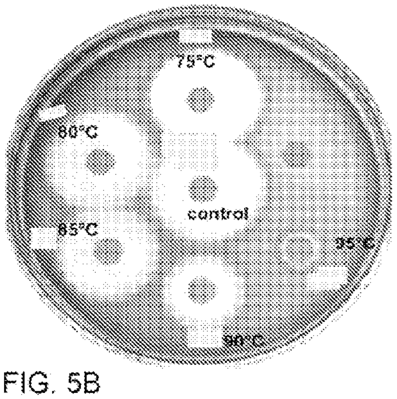
FIGS. 5A-B are photographs showing the heat and pH tolerance of keratinase. (A) A clear zone around the disc-shaped filter paper indicates protease activities. The corresponding heating temperatures are indicated near the filter papers. (B) The corresponding pH values are indicated near the rectangular filter papers.
Figure 5B:
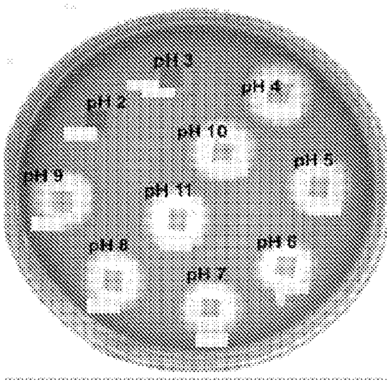

The truncated form of the recombinant keratinase revealed a broad range of proteolytic activities that degraded not only proteins in feathers but also proteins in milk, casein and elastin (FIG. 4). The recombinant keratinase retained activities after being heated up to 95° C. or pre-incubation in an acidic or basic solution (FIGS. 5A-B).

Cloning of *M. taiwanensis* WR-220 Keratinase Gene for Yeast Expression System

The gene of the inhibitory and the catalytic domain of keratinase (spr2261ic) and the gene of the catalytic domain of keratinase (spr2261c) were, respectively, fused with the yeast alpha-factor signal peptide (SEQ ID NO: 15), which allows secretion of keratinase into the culture medium. The constructed plasmids containing spr2261ic and spr2261c were named pHTPY2_spr2261ic and pHTPY2_spr2261c, respectively (FIGS. 10 and 11). The fused gene transcription was under the control of alcohol oxidase 1 promoter (AOX1). The inserted gene were verified by DNA sequencing.

Recombinant Keratinase Production by *P. pastoris* X-33 Strain

Figure 6:
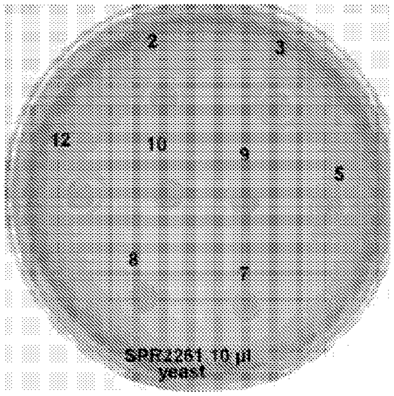
FIG. 6 shows the results of a paper disk-agar diffusion assay for protease activity. The culture supernatants of 8 elected yeast clones (Day 5) were collected for protease activities.
Figure 7:
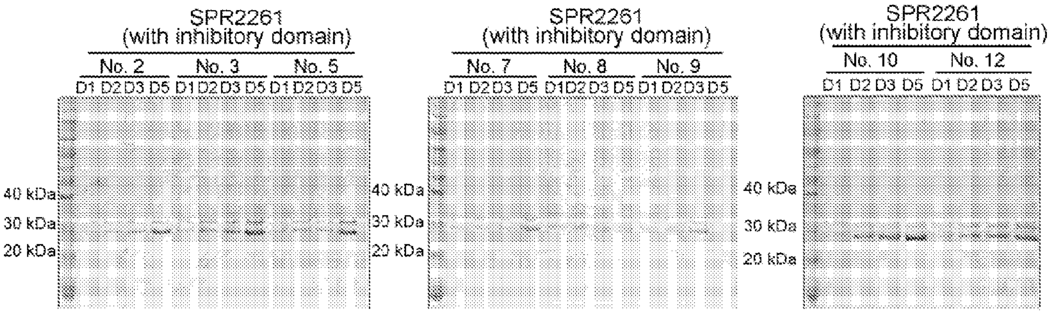
FIG. 7 shows the results of SDS-PAGE electrophoreses of the culture supernatants of 8 elected yeast clones (No. 2, 3, 5, 7, 8, 9, 10 and 12). D1, D2, D3 and D5 denote day 1, 2, 3, and 5 respectively.

Twelve positive colonies containing pHTPY2_spr2261ic were chosen for recombinant keratinase production. Eight of 12 colonies were cultured and 5 out of 8 culture supernatants showed protease activities in a paper disk-agar diffusion assay, indicating that the keratinase was produced (FIG. 6). The SDS-PAGE electrophoreses of the culture supernatants showed two major protein bands (FIG. 7). A subsequent Mass spectrometric characterization revealed that both protein bands contained the catalytic domain of: *M. taiwanensis* keratinase. Based on our experience and crystal structure, we believe that protein in the upper band was the catalytic domain with the linker and 8×His tag and the protein in the lower band was the catalytic domain only. The estimated molecular weight of the protein, which was based on the band position in the SDS-PAGE, indicated that the inhibitory domain was removed during protein production. This result was similar to keratinase production using the *E. coli* expression system. The data suggested that the major secreted protein from the *P. pastoris* with our constructed plasmid was the catalytic domain of *A. taiwanensis* keratinase.

The Requirement of the Inhibitory Domain for Recombinant Keratinase Production

Although the constructed pHTPY2 . . . spr2261ic plasmid contained both the inhibitory domain and the catalytic domain, the secreted protein showed no attachment of N-terminal inhibitory domain. This phenomenon has been observed in *M. taiwanensis* keratinase production using *E. coli* expression system. Furthermore, the constructed pHTPY2_spr2261c plasmid containing no inhibitory domain failed to produce keratinase, suggesting the requirement of the inhibitory domain for protein production even though the final product did not contain the inhibitory domain.

Structural Analysis of *M. taiwanensis* WR-220 Keratinase

Figure 12A:
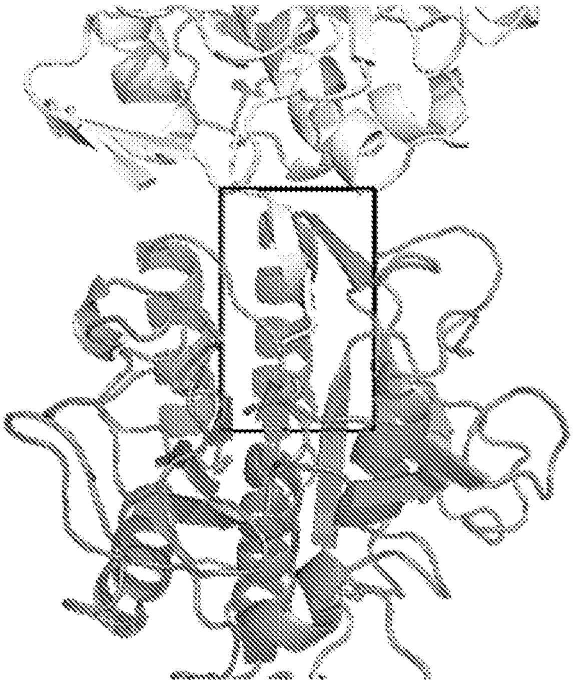
FIGS. 12A-B are cartoon models showing the results of structural studies of *M. taiwanensis* WR-220 keratinase. (A) The structures of two keratinases are colored in light gray and dark gray, respectively. The active site is highlighted in the black box and the key active site residue, Ser224 (referring to SEQ ID NO: 14) is shown as a stick model. The linker region from one of keratinases (light gray) is located in the active site of the other keratinase (dark gray). (B) A close look of the active site of the keratinase. The active site residues (Asp39, His72 and Ser224) and the residues involved in substrate interaction are labeled.
Figure 12B:
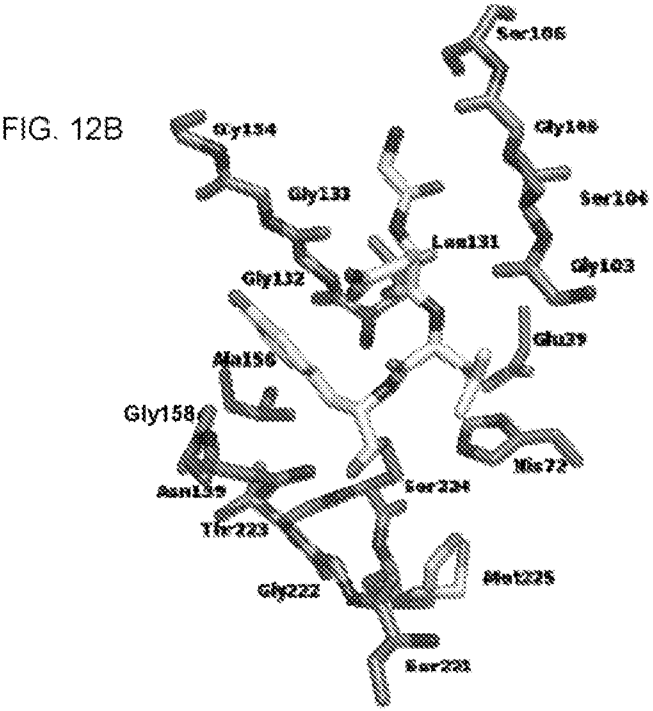

Our crystal structure of *M. taiwanensis* WR-220 keratinase has shown that the part of the linker region connecting the catalytic domain and the His fusion tag is located in the active site of the catalytic domain of the adjacent keratinase (FIG. 12A). This data shows that the Ser221, His72 and Asp39 are the catalytic residues (FIG. 12B; only the catalytic domain residue numbering is used; the first residue is Ala and the second one is Thr; SEQ ID NO: 14). Moreover, the structural analysis showed that Gly103, Ser104, Gly105, Ser106, Leu131, Gly132, Gly133, Gly134, Ala156, Gly158, Asn159, Ser221, Gly222, Thr223 and Met225 are involved in substrate interaction (FIG. 12B). The sequences shown in FIGS. 10B, 11B are produced from yeast system. The structural analyses were performed using keratinase produced by *E. coli*, expression system. The linker sequence used in yeast system expression system was GNLYFQS (SEQ ID NO: 16). In *E. coli* system, the residue G was replaced by E.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A fusion gene comprising:

(a) a first DNA sequence encoding a protein secretion signal peptide, located at the N-terminus of the fusion gene;

(b) a second DNA sequence encoding an inhibitory domain of *Meiothermus taiwanensis* WR-220 keratinase, linked in translation frame with the first DNA sequence; and (c) a third DNA sequence encoding a catalytic domain of *M. taiwanensis* WR-220 keratinase, linked in translation frame with the second DNA sequence, wherein the fusion gene is a non-naturally occurring chimeric DNA.

2. The fusion gene of claim 1, wherein the first DNA sequence encodes a yeast alpha-factor signal peptide.

3. A protein expression vector comprising:

(a) the fusion gene of claim 1; and (b) a promoter, linked in translation frame with the fusion gene.

4. The protein expression vector of claim 3, wherein the promoter is selected from the group consisting of alcohol oxidase (AOX) promoter, glyceraldehyde phosphate dehydrogenase promoter, translational elongation factor 1-α promoter, $Na^+$-coupled phosphate symproter promoter, and formaldehyde dehydrogenase promoter.

5. A host cell comprising the expression vector of claim 3.

6. A cell culture comprising:

(a) an artificial medium;

(b) the host cell of claim 5, the host cell secreting the catalytic domain of *M. taiwanensis* WR-220 keratinase into the artificial medium.

7. An isolated protease comprising a catalytic domain of *M. taiwanensis* WR-220 keratinase, the protease lacking an inhibitory domain of *M. taiwanensis* WR-220 keratinase, and being in a dosage form of tablet, caplet, pellet, capsule, granule, pill, powder or sachet, or in a dosage form of solution without containing a cell culture supplement.

8. The protease of claim 7, which comprises an amino acid sequence having at least 95% identity to SEQ ID NO: 14.

9. A method for degrading a proteinaceous material, comprising:

exposing the proteinaceous material to an effective amount of the isolated protease of claim 7.

10. The method of claim 9, wherein the protease is pretreated at a temperature above 40° C. but below 95° C. and remains its activity.

11. The method of claim 9, wherein the proteinaceous material is selected from the group consisting of animal feed, food, milk, casein, elastin, skin, hair, wool, silk, nails, scales, fiber, leather, and feathers.

12. The method of claim 9, wherein the protease is pretreated with a solution having a pH value ranging from 3 to 10 and remains its activity.

13. A method for preparation of a catalytic domain of *M. taiwanensis* WR-220 keratinase, comprising:

(ai) growing the host cell of claim 5 in a culture medium under conditions that permits expression of *M. taiwanensis* WR-220 keratinase and secretion of the catalytic domain thereof into the medium; or (aii) growing a host cell transformed with an expression plasmid comprising a DNA insert encoding an inhibitory domain and a catalytic domain of *M. taiwanensis* WR-220 keratinase under conditions that permits expression of *M. taiwanensis* WR-220 keratinase and secretion of the catalytic domain thereof into the medium; and (b) removing the host cell to obtain a supernatant containing the catalytic domain of the *M. taiwanensis* WR-220 keratinase; and (c) isolating the catalytic domain from the supernatant or drying the supernatant to obtain the catalytic domain in solid form.

14. The method of claim 13, wherein the inhibitory domain comprises an amino acid sequence having at least 95% identity to SEQ ID NO: 13; and the catalytic domain comprises an amino acid sequence having at least 95% identity to SEQ ID NO: 14.

15. The fusion gene of claim 1, wherein the inhibitory domain comprises an amino acid sequence having at least 95% identity to SEQ ID NO: 13; and the catalytic domain comprises an amino acid sequence having at least 95% identity to SEQ ID NO: 14.

16. An isolated protease comprising the catalytic domain of *M. taiwanensis* WR-220 keratinase secreted by the cell culture of claim 6.

17. The isolated protease of claim 16, which is in a dosage form of tablet, caplet, pellet, capsule, granule, pill, powder, or sachet, or in a dosage form of solution without containing a cell culture supplement.

18. A method for degrading a proteinaceous material, comprising:

exposing the proteinaceous material to an effective amount of the protease of claim 8.

19. A protein expression vector comprising:

(a) the fusion gene of claim 2; and (b) a promoter, linked in translation frame with the fusion gene.

20. A protein expression vector comprising:

(a) the fusion gene of claim 15; and (b) a promoter, linked in translation frame with the fusion gene.

* * * * *

SEQUENCE LISTING

```
<160> NUMBER OF SEQ ID NOS: 34

<210> SEQ ID NO 1
<211> LENGTH: 39
<212> TYPE: DNA
<213> ORGANISM: Artificial Sequence
<220> FEATURE:
<223> OTHER INFORMATION: forward primer

<400> SEQUENCE: 1

ttaagaagga gatataccat gctagccccg gtgctagga                          39


<210> SEQ ID NO 2
<211> LENGTH: 48
<212> TYPE: DNA
<213> ORGANISM: Artificial Sequence
<220> FEATURE:
<223> OTHER INFORMATION: reverse primer

<400> SEQUENCE: 2

gattggaagt agaggttctc tgcgtaattg ctgtacagca gcaggttg                48


<210> SEQ ID NO 3
<211> LENGTH: 1209
<212> TYPE: DNA
<213> ORGANISM: Meiothermus taiwanensis sp. nov.

<400> SEQUENCE: 3

atgtaccgtc tagtttggat cgcgctgttg ttgttactgg catcctgcgg aaaccgtgcg    60

acccccgaca acctagcccc ggtgctagga ctggataacc ccaacgttat ccaggggcag   120

tacattgtgg tctacaagga tgatgccaac gtgctgccca ccctgcaaag cctgaaagcc   180

gctttagatg ggggtgtaac ccttcagcgg gaactggaaa gcctggggct ggcacccgac   240

gccagggttg agcaggttta caccgctgct ctgctggggc ttgcggcccg gctatcaccc   300
```

-continued

```
gagaatttag ccgcgctgcg gcaggatccc cgggtggcct acatcgaggc cgaccaggtc    360
atgagcatca gcgccaccca gaccggtgcg acctggggcc tggatcgcat agaccagcgc    420
accctacccc tcagcggtac cttcacctac agcaacacgg gcagcggcgt gaacgcctac    480
atcatcgata ccggtatccg ggtgagccac agcgagtttg gcggtcgggc cacggcggtt    540
ttcgacgcta ttggagacgg ccagaatggc aacgactgca acggccatgg cacccatgtg    600
gctggaacgg taggcggcac ggtctacggc gtagccaaaa gcgtgcggtt gtacgcggtg    660
cgggtgctta attgcagcgg ctcgggcagc aactcgggcg taattgccgg ggtggactgg    720
gtgcggcaga atgcccggag gccagcggta gccaacatga gcctgggtgg gggggcctcg    780
agcgccctcg ataccgcggt caataacgcc atcaacgccg ggattacctt tgccctggcc    840
gcaggtaaca gcaaccgcga cgcctgccag ttctcgccag cccgcgtcac tgcaggcatt    900
accgtggggg ccaccacctc caccgacgcc agggcctcct attccaacta cggtagctgc    960
ctcgacctct tcgcccccgg ctcttccatc acctcggcct ggattagcag cgacacctcg   1020
accaacacca tcagcggaac ctcgatggcc accccccatg tggccggggt agcggctttg   1080
tacctgcaaa gcaaccccag tgccagcccc gccaccgtgc gcaacgccat tgtgggcaac   1140
gccacttcgg gtgtggtgag caacgccggg cggcgttcgc ccaacctgct gctgtacagc   1200
aattactga                                                           1209
```

```
<210> SEQ ID NO 4
<211> LENGTH: 402
<212> TYPE: PRT
<213> ORGANISM: Meiothermus taiwanensis sp. nov.

<400> SEQUENCE: 4

Met Tyr Arg Leu Val Trp Ile Ala Leu Leu Leu Leu Leu Ala Ser Cys
1               5                   10                  15

Gly Asn Arg Ala Thr Pro Asp Asn Leu Ala Pro Val Leu Gly Leu Asp
            20                  25                  30

Asn Pro Asn Val Ile Gln Gly Gln Tyr Ile Val Val Tyr Lys Asp Asp
        35                  40                  45

Ala Asn Val Leu Pro Thr Leu Gln Ser Leu Lys Ala Ala Leu Asp Gly
    50                  55                  60

Gly Val Thr Leu Gln Arg Glu Leu Glu Ser Leu Gly Leu Ala Pro Asp
65                  70                  75                  80

Ala Arg Val Glu Gln Val Tyr Thr Ala Ala Leu Leu Gly Leu Ala Ala
                85                  90                  95

Arg Leu Ser Pro Glu Asn Leu Ala Ala Leu Arg Gln Asp Pro Arg Val
            100                 105                 110

Ala Tyr Ile Glu Ala Asp Gln Val Met Ser Ile Ser Ala Thr Gln Thr
        115                 120                 125

Gly Ala Thr Trp Gly Leu Asp Arg Ile Asp Gln Arg Thr Leu Pro Leu
    130                 135                 140

Ser Gly Thr Phe Thr Tyr Ser Asn Thr Gly Ser Gly Val Asn Ala Tyr
145                 150                 155                 160

Ile Ile Asp Thr Gly Ile Arg Val Ser His Ser Glu Phe Gly Gly Arg
                165                 170                 175

Ala Thr Ala Val Phe Asp Ala Ile Gly Asp Gly Gln Asn Gly Asn Asp
            180                 185                 190

Cys Asn Gly His Gly Thr His Val Ala Gly Thr Val Gly Gly Thr Val
        195                 200                 205
```

-continued

```
Tyr Gly Val Ala Lys Ser Val Arg Leu Tyr Ala Val Arg Val Leu Asn
    210                 215                 220

Cys Ser Gly Ser Gly Ser Asn Ser Gly Val Ile Ala Gly Val Asp Trp
225                 230                 235                 240

Val Arg Gln Asn Ala Arg Arg Pro Ala Val Ala Asn Met Ser Leu Gly
                245                 250                 255

Gly Gly Ala Ser Ser Ala Leu Asp Thr Ala Val Asn Asn Ala Ile Asn
            260                 265                 270

Ala Gly Ile Thr Phe Ala Leu Ala Ala Gly Asn Ser Asn Arg Asp Ala
        275                 280                 285

Cys Gln Phe Ser Pro Ala Arg Val Thr Ala Gly Ile Thr Val Gly Ala
    290                 295                 300

Thr Thr Ser Thr Asp Ala Arg Ala Ser Tyr Ser Asn Tyr Gly Ser Cys
305                 310                 315                 320

Leu Asp Leu Phe Ala Pro Gly Ser Ser Ile Thr Ser Ala Trp Ile Ser
                325                 330                 335

Ser Asp Thr Ser Thr Asn Thr Ile Ser Gly Thr Ser Met Ala Thr Pro
            340                 345                 350

His Val Ala Gly Val Ala Ala Leu Tyr Leu Gln Ser Asn Pro Ser Ala
        355                 360                 365

Ser Pro Ala Thr Val Arg Asn Ala Ile Val Gly Asn Ala Thr Ser Gly
    370                 375                 380

Val Val Ser Asn Ala Gly Arg Arg Ser Pro Asn Leu Leu Leu Tyr Ser
385                 390                 395                 400

Asn Tyr


<210> SEQ ID NO 5
<211> LENGTH: 1203
<212> TYPE: DNA
<213> ORGANISM: Meiothermus taiwanensis sp. nov.

<400> SEQUENCE: 5

atgctagccc cggtgctagg actggataac cccaacgtta tccaggggca gtacattgtg      60

gtctacaagg atgatgccaa cgtgctgccc accctgcaaa gcctgaaagc cgctttagat     120

gggggtgtaa cccttcagcg ggaactggaa agcctggggc tggcacccga cgccagggtt     180

gagcaggttt acaccgctgc tctgctgggg cttgcggccc ggctatcacc cgagaattta     240

gccgcgctgc ggcaggatcc ccgggtggcc tacatcgagg ccgaccaggt catgagcatc     300

agcgccaccc agaccggtgc gacctggggc ctggatcgca tagaccagcg caccctaccc     360

ctcagcggta ccttcaccta cagcaacacg ggcagcggcg tgaacgccta catcatcgat     420

accggtatcc gggtgagcca cagcgagttt ggcggtcggg ccacggcggt tttcgacgct     480

attggagacg gccagaatgg caacgactgc aacggccatg gcacccatgt ggctggaacg     540

gtaggcggca cggtctacgg cgtagccaaa agcgtgcggt tgtacgcggt gcgggtgctt     600

aattgcagcg gctcgggcag caactcgggc gtaattgccg gggtggactg ggtgcggcag     660

aatgcccgga ggccagcggt agccaacatg agcctgggtg ggggggcctc gagcgccctc     720

gataccgcgg tcaataacgc catcaacgcc gggattacct ttgccctggc cgcaggtaac     780

agcaaccgcg acgcctgcca gttctcgcca gcccgcgtca ctgcaggcat taccgtgggg     840

gccaccacct ccaccgacgc cagggcctcc tattccaact acggtagctg cctcgacctc     900

ttcgcccccg gctcttccat cacctcggcc tggattagca gcgacacctc gaccaacacc     960

atcagcggaa cctcgatggc cacccccat gtggccgggg tagcggcttt gtacctgcaa    1020
```

```
agcaacccca gtgccagccc cgccaccgtg cgcaacgcca ttgtgggcaa cgccacttcg   1080

ggtgtggtga gcaacgccgg gcggcgttcg cccaacctgc tgctgtacag caattacgag   1140

aacctctact tccaatcgca ccatcatcac caccattgga gccatccgca gtttgaaaaa   1200

tag                                                                 1203


<210> SEQ ID NO 6
<211> LENGTH: 400
<212> TYPE: PRT
<213> ORGANISM: Meiothermus taiwanensis sp. nov.

<400> SEQUENCE: 6

Met Leu Ala Pro Val Leu Gly Leu Asp Asn Pro Asn Val Ile Gln Gly
1               5                   10                  15

Gln Tyr Ile Val Val Tyr Lys Asp Asp Ala Asn Val Leu Pro Thr Leu
            20                  25                  30

Gln Ser Leu Lys Ala Ala Leu Asp Gly Gly Val Thr Leu Gln Arg Glu
        35                  40                  45

Leu Glu Ser Leu Gly Leu Ala Pro Asp Ala Arg Val Glu Gln Val Tyr
    50                  55                  60

Thr Ala Ala Leu Leu Gly Leu Ala Ala Arg Leu Ser Pro Glu Asn Leu
65                  70                  75                  80

Ala Ala Leu Arg Gln Asp Pro Arg Val Ala Tyr Ile Glu Ala Asp Gln
                85                  90                  95

Val Met Ser Ile Ser Ala Thr Gln Thr Gly Ala Thr Trp Gly Leu Asp
            100                 105                 110

Arg Ile Asp Gln Arg Thr Leu Pro Leu Ser Gly Thr Phe Thr Tyr Ser
        115                 120                 125

Asn Thr Gly Ser Gly Val Asn Ala Tyr Ile Ile Asp Thr Gly Ile Arg
    130                 135                 140

Val Ser His Ser Glu Phe Gly Gly Arg Ala Thr Ala Val Phe Asp Ala
145                 150                 155                 160

Ile Gly Asp Gly Gln Asn Gly Asn Asp Cys Asn Gly His Gly Thr His
                165                 170                 175

Val Ala Gly Thr Val Gly Gly Thr Val Tyr Gly Val Ala Lys Ser Val
            180                 185                 190

Arg Leu Tyr Ala Val Arg Val Leu Asn Cys Ser Gly Ser Gly Ser Asn
        195                 200                 205

Ser Gly Val Ile Ala Gly Val Asp Trp Val Arg Gln Asn Ala Arg Arg
    210                 215                 220

Pro Ala Val Ala Asn Met Ser Leu Gly Gly Gly Ala Ser Ser Ala Leu
225                 230                 235                 240

Asp Thr Ala Val Asn Asn Ala Ile Asn Ala Gly Ile Thr Phe Ala Leu
                245                 250                 255

Ala Ala Gly Asn Ser Asn Arg Asp Ala Cys Gln Phe Ser Pro Ala Arg
            260                 265                 270

Val Thr Ala Gly Ile Thr Val Gly Ala Thr Thr Ser Thr Asp Ala Arg
        275                 280                 285

Ala Ser Tyr Ser Asn Tyr Gly Ser Cys Leu Asp Leu Phe Ala Pro Gly
    290                 295                 300

Ser Ser Ile Thr Ser Ala Trp Ile Ser Ser Asp Thr Ser Thr Asn Thr
305                 310                 315                 320

Ile Ser Gly Thr Ser Met Ala Thr Pro His Val Ala Gly Val Ala Ala
                325                 330                 335
```

-continued

Leu Tyr Leu Gln Ser Asn Pro Ser Ala Ser Pro Ala Thr Val Arg Asn
340 345 350

Ala Ile Val Gly Asn Ala Thr Ser Gly Val Val Ser Asn Ala Gly Arg
355 360 365

Arg Ser Pro Asn Leu Leu Leu Tyr Ser Asn Tyr Glu Asn Leu Tyr Phe
370 375 380

Gln Ser His His His His His His Trp Ser His Pro Gln Phe Glu Lys
385 390 395 400

<210> SEQ ID NO 7
<211> LENGTH: 4666
<212> TYPE: DNA
<213> ORGANISM: Artificial Sequence
<220> FEATURE:
<223> OTHER INFORMATION: pHTPY2_spr2261ic

<400> SEQUENCE: 7
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg atgagatttc cttctatttt 960
tactgctgtt ttattcgcag catcctccgc attagctgct ccagtcaaca ctacaacaga 1020
agatgaaacg gcacaaattc cggctgaagc tgtcatcggt tactcagatt tagaagggga 1080
tttcgatgtt gctgttttgc cattttccaa cagcacaaat aacgggttat tgtttataaa 1140
tactactatt gccagcattg ctgctaaaga agaaggggta tctctcgaaa aaagagaggc 1200
tgaagcagaa ggaattggag tggcaggaat gctagccccg gtgctaggac tggataaccc 1260
caacgttatc caggggcagt acattgtggt ctacaaggat gatgccaacg tgctgcccac 1320
cctgcaaagc ctgaaagccg ctttagatgg gggtgtaacc cttcagcggg aactggaaag 1380
cctggggctg gcacccgacg ccagggttga gcaggtttac accgctgctc tgctggggct 1440
tgcggcccgg ctatcacccg agaatttagc cgcgctgcgg caggatcccc gggtggccta 1500
catcgaggcc gaccaggtca tgagcatcag cgccacccag accggtgcga cctggggcct 1560
ggatcgcata gaccagcgca ccctacccct cagcggtacc ttcacctaca gcaacacggg 1620
cagcggcgtg aacgcctaca tcatcgatac cggtatccgg gtgagccaca gcgagtttgg 1680

-continued

```
cggtcgggcc acggcggttt tcgacgctat tggagacggc cagaatggca acgactgcaa   1740
cggccatggc acccatgtgg ctggaacggt aggcggcacg gtctacggcg tagccaaaag   1800
cgtgcggttg tacgcggtgc gggtgcttaa ttgcagcggc tcgggcagca actcgggcgt   1860
aattgccggg gtggactggg tgcggcagaa tgcccggagg ccagcggtag ccaacatgag   1920
cctgggtggg ggggcctcga gcgccctcga taccgcggtc aataacgcca tcaacgccgg   1980
gattaccttt gccctggccg caggtaacag caaccgcgac gcctgccagt tctcgccagc   2040
ccgcgtcact gcaggcatta ccgtgggggc caccacctcc accgacgcca gggcctccta   2100
ttccaactac ggtagctgcc tcgacctctt cgcccccggc tcttccatca cctcggcctg   2160
gattagcagc gacacctcga ccaacaccat cagcggaacc tcgatggcca ccccccatgt   2220
ggccggggta gcggctttgt acctgcaaag caaccccagt gccagccccg ccaccgtgcg   2280
caacgccatt gtgggcaacg ccacttcggg tgtggtgagc aacgccgggc ggcgttcgcc   2340
caacctgctg ctgtacagca attacgggaa cctctacttc caatcgcatc atcatcatca   2400
tcatcaccat tgagtttgta gccttagaca tgactgttcc tcagttcaag ttgggcactt   2460
acgagaagac cggtcttgct agattctaat caagaggatg tcagaatgcc atttgcctga   2520
gagatgcagg cttcattttt gatacttttt tatttgtaac ctatatagta taggattttt   2580
tttgtcattt tgtttcttct cgtacgagct tgctcctgat cagcctatct cgcagctgat   2640
gaatatcttg tggtaggggt ttgggaaaat cattcgagtt tgatgttttt cttggtattt   2700
cccactcctc ttcagagtac agaagattaa gtgagacctt cgtttgtgcg gatcccccac   2760
acaccatagc ttcaaaatgt ttctactcct tttttactct tccagatttt ctcggactcc   2820
gcgcatcgcc gtaccacttc aaaacaccca agcacagcat actaaatttt ccctctttct   2880
tcctctaggg tgtcgttaat tacccgtact aaaggtttgg aaaagaaaaa agagaccgcc   2940
tcgtttcttt ttcttcgtcg aaaaaggcaa taaaaatttt tatcacgttt ctttttcttg   3000
aaattttttt ttttagtttt tttctctttc agtgacctcc attgatattt aagttaataa   3060
acggtcttca atttctcaag tttcagtttc atttttcttg ttctattaca acttttttta   3120
cttcttgttc attagaaaga aagcatagca atctaatcta aggggcggtg ttgacaatta   3180
atcatcggca tagtatatcg gcatagtata atacgacaag gtgaggaact aaaccatggc   3240
caagttgacc agtgccgttc cggtgctcac cgcgcgcgac gtcgccggag cggtcgagtt   3300
ctggaccgac cggctcgggt tctcccggga cttcgtggag gacgacttcg ccggtgtggt   3360
ccgggacgac gtgaccctgt tcatcagcgc ggtccaggac caggtggtgc cggacaacac   3420
cctggcctgg gtgtgggtgc gcggcctgga cgagctgtac gccgagtggt cggaggtcgt   3480
gtccacgaac ttccgggacg cctccgggcc ggccatgacc gagatcggcg agcagccgtg   3540
ggggcgggag ttcgccctgc gcgacccggc cggcaactgc gtgcacttcg tggccgagga   3600
gcaggactga cacgtccgac ggcggcccac gggtcccagg cctcggagat ccgtcccccct  3660
tttcctttgt cgatatcatg taattagtta tgtcacgctt acattcacgc cctcccccca   3720
catccgctct aaccgaaaag gaaggagtta gacaacctga agtctaggtc cctatttatt   3780
tttttatagt tatgttagta ttaagaacgt tatttatatt tcaaattttt cttttttttc   3840
tgtacagacg cgtgtacgca tgtaacatta tactgaaaac cttgcttgag aaggttttgg   3900
gacgctcgaa ggctttaatt tgcaagctgg agaccaacat gtgagcaaaa ggccagcaaa   3960
aggccaggaa ccgtaaaaag gccgcgttgc tggcgttttt ccataggctc cgcccccctg   4020
acgagcatca caaaaatcga cgctcaagtc agaggtggcg aaacccgaca ggactataaa   4080
```

-continued

```
gataccaggc gtttccccct ggaagctccc tcgtgcgctc tcctgttccg accctgccgc   4140

ttaccggata cctgtccgcc tttctccctt cgggaagcgt ggcgctttct caatgctcac   4200

gctgtaggta tctcagttcg gtgtaggtcg ttcgctccaa gctgggctgt gtgcacgaac   4260

cccccgttca gcccgaccgc tgcgccttat ccggtaacta tcgtcttgag tccaacccgg   4320

taagacacga cttatcgcca ctggcagcag ccactggtaa caggattagc agagcgaggt   4380

atgtaggcgg tgctacagag ttcttgaagt ggtggcctaa ctacggctac actagaagga   4440

cagtatttgg tatctgcgct ctgctgaagc cagttacctt cggaaaaaga gttggtagct   4500

cttgatccgg caaacaaacc accgctggta gcggtggttt ttttgtttgc aagcagcaga   4560

ttacgcgcag aaaaaaagga tctcaagaag atcctttgat cttttctacg gggtctgacg   4620

ctcagtggaa cgaaaactca cgttaaggga ttttggtcat gagatc                  4666
```

```
<210> SEQ ID NO 8
<211> LENGTH: 490
<212> TYPE: PRT
<213> ORGANISM: Artificial Sequence
<220> FEATURE:
<223> OTHER INFORMATION: pHTPY2_spr2261ic corresponding expressed
      protein

<400> SEQUENCE: 8

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Gly Ile Gly Val Ala Gly
                85                  90                  95

Met Leu Ala Pro Val Leu Gly Leu Asp Asn Pro Asn Val Ile Gln Gly
            100                 105                 110

Gln Tyr Ile Val Val Tyr Lys Asp Asp Ala Asn Val Leu Pro Thr Leu
        115                 120                 125

Gln Ser Leu Lys Ala Ala Leu Asp Gly Gly Val Thr Leu Gln Arg Glu
    130                 135                 140

Leu Glu Ser Leu Gly Leu Ala Pro Asp Ala Arg Val Glu Gln Val Tyr
145                 150                 155                 160

Thr Ala Ala Leu Leu Gly Leu Ala Ala Arg Leu Ser Pro Glu Asn Leu
                165                 170                 175

Ala Ala Leu Arg Gln Asp Pro Arg Val Ala Tyr Ile Glu Ala Asp Gln
            180                 185                 190

Val Met Ser Ile Ser Ala Thr Gln Thr Gly Ala Thr Trp Gly Leu Asp
        195                 200                 205

Arg Ile Asp Gln Arg Thr Leu Pro Leu Ser Gly Thr Phe Thr Tyr Ser
    210                 215                 220

Asn Thr Gly Ser Gly Val Asn Ala Tyr Ile Ile Asp Thr Gly Ile Arg
225                 230                 235                 240

Val Ser His Ser Glu Phe Gly Gly Arg Ala Thr Ala Val Phe Asp Ala
                245                 250                 255
```

-continued

```
Ile Gly Asp Gly Gln Asn Gly Asn Asp Cys Asn Gly His Gly Thr His
            260                 265                 270

Val Ala Gly Thr Val Gly Gly Thr Val Tyr Gly Val Ala Lys Ser Val
        275                 280                 285

Arg Leu Tyr Ala Val Arg Val Leu Asn Cys Ser Gly Ser Gly Ser Asn
    290                 295                 300

Ser Gly Val Ile Ala Gly Val Asp Trp Val Arg Gln Asn Ala Arg Arg
305                 310                 315                 320

Pro Ala Val Ala Asn Met Ser Leu Gly Gly Gly Ala Ser Ser Ala Leu
                325                 330                 335

Asp Thr Ala Val Asn Asn Ala Ile Asn Ala Gly Ile Thr Phe Ala Leu
            340                 345                 350

Ala Ala Gly Asn Ser Asn Arg Asp Ala Cys Gln Phe Ser Pro Ala Arg
        355                 360                 365

Val Thr Ala Gly Ile Thr Val Gly Ala Thr Thr Ser Thr Asp Ala Arg
    370                 375                 380

Ala Ser Tyr Ser Asn Tyr Gly Ser Cys Leu Asp Leu Phe Ala Pro Gly
385                 390                 395                 400

Ser Ser Ile Thr Ser Ala Trp Ile Ser Ser Asp Thr Ser Thr Asn Thr
                405                 410                 415

Ile Ser Gly Thr Ser Met Ala Thr Pro His Val Ala Gly Val Ala Ala
            420                 425                 430

Leu Tyr Leu Gln Ser Asn Pro Ser Ala Ser Pro Ala Thr Val Arg Asn
        435                 440                 445

Ala Ile Val Gly Asn Ala Thr Ser Gly Val Val Ser Asn Ala Gly Arg
    450                 455                 460

Arg Ser Pro Asn Leu Leu Leu Tyr Ser Asn Tyr Gly Asn Leu Tyr Phe
465                 470                 475                 480

Gln Ser His His His His His His His His
                485                 490


<210> SEQ ID NO 9
<211> LENGTH: 4363
<212> TYPE: DNA
<213> ORGANISM: Artificial Sequence
<220> FEATURE:
<223> OTHER INFORMATION: pHTPY2_spr2261c

<400> SEQUENCE: 9

agatctaaca tccaaagacg aaaggttgaa tgaaaccttt ttgccatccg acatccacag     60

gtccattctc acacataagt gccaaacgca acaggagggg atacactagc agcagaccgt    120

tgcaaacgca ggacctccac tcctcttctc ctcaacaccc acttttgcca tcgaaaaacc    180

agcccagtta ttgggcttga ttggagctcg ctcattccaa ttccttctat taggctacta    240

acaccatgac tttattagcc tgtctatcct ggcccccctg gcgaggttca tgtttgttta    300

tttccgaatg caacaagctc cgcattacac ccgaacatca ctccagatga gggctttctg    360

agtgtggggt caaatagttt catgttcccc aaatggccca aaactgacag tttaaacgct    420

gtcttggaac ctaatatgac aaaagcgtga tctcatccaa gatgaactaa gtttggttcg    480

ttgaaatgct aacggccagt tggtcaaaaa gaaacttcca aaagtcggca taccgtttgt    540

cttgtttggt attgattgac gaatgctcaa aaataatctc attaatgctt agcgcagtct    600

ctctatcgct tctgaacccc ggtgcacctg tgccgaaacg caaatgggga aacacccgct    660

ttttggatga ttatgcattg tctccacatt gtatgcttcc aagattctgg tgggaatact    720
```

-continued

```
gctgatagcc taacgttcat gatcaaaatt taactgttct aacccctact tgacagcaat    780
atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaaacg atgagatttc cttctatttt    960
tactgctgtt ttattcgcag catcctccgc attagctgct ccagtcaaca ctacaacaga   1020
agatgaaacg gcacaaattc cggctgaagc tgtcatcggt tactcagatt tagaagggga   1080
tttcgatgtt gctgttttgc cattttccaa cagcacaaat aacgggttat tgtttataaa   1140
tactactatt gccagcattg ctgctaaaga agaaggggta tctctcgaaa aaagagaggc   1200
tgaagcagaa ggaattggag tggcaggagc cacccagacc ggtgcgacct ggggcctgga   1260
tcgcatagac cagcgcaccc tacccctcag cggtaccttc acctacagca acacgggcag   1320
cggcgtgaac gcctacatca tcgataccgg tatccgggtg agccacagcg agtttggcgg   1380
tcgggccacg gcggttttcg acgctattgg agacggccag aatggcaacg actgcaacgg   1440
ccatggcacc catgtggctg gaacggtagg cggcacggtc tacggcgtag ccaaaagcgt   1500
gcggttgtac gcggtgcggg tgcttaattg cagcggctcg ggcagcaact cgggcgtaat   1560
tgccggggtg gactgggtgc ggcagaatgc ccggaggcca gcggtagcca acatgagcct   1620
gggtgggggg gcctcgagcg ccctcgatac cgcggtcaat aacgccatca acgccgggat   1680
tacctttgcc ctggccgcag gtaacagcaa ccgcgacgcc tgccagttct cgccagcccg   1740
cgtcactgca ggcattaccg tgggggccac cacctccacc gacgccaggg cctcctattc   1800
caactacggt agctgcctcg acctcttcgc ccccggctct tccatcacct cggcctggat   1860
tagcagcgac acctcgacca acaccatcag cggaacctcg atggccaccc cccatgtggc   1920
cggggtagcg gctttgtacc tgcaaagcaa ccccagtgcc agccccgcca ccgtgcgcaa   1980
cgccattgtg ggcaacgcca cttcgggtgt ggtgagcaac gccgggcggc gttcgcccaa   2040
cctgctgctg tacagcaatt acgggaacct ctacttccaa tcgcatcatc atcatcatca   2100
tcaccattga gtttgtagcc ttagacatga ctgttcctca gttcaagttg ggcacttacg   2160
agaagaccgg tcttgctaga ttctaatcaa gaggatgtca gaatgccatt tgcctgagag   2220
atgcaggctt catttttgat actttttttat ttgtaaccta tatagtatag gatttttttt   2280
gtcattttgt ttcttctcgt acgagcttgc tcctgatcag cctatctcgc agctgatgaa   2340
tatcttgtgg taggggtttg ggaaaatcat tcgagtttga tgtttttctt ggtatttccc   2400
actcctcttc agagtacaga agattaagtg agaccttcgt ttgtgcggat cccccacaca   2460
ccatagcttc aaaatgtttc tactcctttt ttactcttcc agattttctc ggactccgcg   2520
catcgccgta ccacttcaaa acacccaagc acagcatact aaattttccc tctttcttcc   2580
tctagggtgt cgttaattac ccgtactaaa ggtttggaaa agaaaaaaga gaccgcctcg   2640
tttctttttc ttcgtcgaaa aaggcaataa aaatttttat cacgtttctt tttcttgaaa   2700
ttttttttt tagtttttttt ctctttcagt gacctccatt gatatttaag ttaataaacg   2760
gtcttcaatt tctcaagttt cagtttcatt tttcttgttc tattacaact tttttactt    2820
cttgttcatt agaaagaaag catagcaatc taatctaagg ggcggtgttg acaattaatc   2880
atcggcatag tatatcggca tagtataata cgacaaggtg aggaactaaa ccatggccaa   2940
gttgaccagt gccgttccgg tgctcaccgc gcgcgacgtc gccggagcgg tcgagttctg   3000
gaccgaccgg ctcgggttct cccgggactt cgtggaggac gacttcgccg gtgtggtccg   3060
```

-continued

```
ggacgacgtg accctgttca tcagcgcggt ccaggaccag gtggtgccgg acaacaccct   3120
ggcctgggtg tgggtgcgcg gcctggacga gctgtacgcc gagtggtcgg aggtcgtgtc   3180
cacgaacttc cgggacgcct ccgggccggc catgaccgag atcggcgagc agccgtgggg   3240
gcgggagttc gccctgcgcg acccggccgg caactgcgtg cacttcgtgg ccgaggagca   3300
ggactgacac gtccgacggc ggcccacggg tcccaggcct cggagatccg tccccctttt   3360
cctttgtcga tatcatgtaa ttagttatgt cacgcttaca ttcacgccct ccccccacat   3420
ccgctctaac cgaaaaggaa ggagttagac aacctgaagt ctaggtccct atttattttt   3480
ttatagttat gttagtatta agaacgttat ttatatttca aatttttctt ttttttctgt   3540
acagacgcgt gtacgcatgt aacattatac tgaaaacctt gcttgagaag gttttgggac   3600
gctcgaaggc tttaatttgc aagctggaga ccaacatgtg agcaaaaggc cagcaaaagg   3660
ccaggaaccg taaaaaggcc gcgttgctgg cgtttttcca taggctccgc ccccctgacg   3720
agcatcacaa aaatcgacgc tcaagtcaga ggtggcgaaa cccgacagga ctataaagat   3780
accaggcgtt tccccctgga agctccctcg tgcgctctcc tgttccgacc ctgccgctta   3840
ccggatacct gtccgccttt ctcccttcgg gaagcgtggc gctttctcaa tgctcacgct   3900
gtaggtatct cagttcggtg taggtcgttc gctccaagct gggctgtgtg cacgaacccc   3960
ccgttcagcc cgaccgctgc gccttatccg gtaactatcg tcttgagtcc aacccggtaa   4020
gacacgactt atcgccactg gcagcagcca ctggtaacag gattagcaga gcgaggtatg   4080
taggcggtgc tacagagttc ttgaagtggt ggcctaacta cggctacact agaaggacag   4140
tatttggtat ctgcgctctg ctgaagccag ttaccttcgg aaaaagagtt ggtagctctt   4200
gatccggcaa acaaaccacc gctggtagcg gtggtttttt tgtttgcaag cagcagatta   4260
cgcgcagaaa aaaaggatct caagaagatc ctttgatctt ttctacgggg tctgacgctc   4320
agtggaacga aaactcacgt taagggattt tggtcatgag atc                     4363
```

```
<210> SEQ ID NO 10
<211> LENGTH: 389
<212> TYPE: PRT
<213> ORGANISM: Artificial Sequence
<220> FEATURE:
<223> OTHER INFORMATION: pHTPY2_spr2261c corresponding expressed protein
      sequence

<400> SEQUENCE: 10

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Gly Ile Gly Val Ala Gly
                85                  90                  95

Ala Thr Gln Thr Gly Ala Thr Trp Gly Leu Asp Arg Ile Asp Gln Arg
            100                 105                 110

Thr Leu Pro Leu Ser Gly Thr Phe Thr Tyr Ser Asn Thr Gly Ser Gly
        115                 120                 125
```

-continued

```
Val Asn Ala Tyr Ile Ile Asp Thr Gly Ile Arg Val Ser His Ser Glu
    130                 135                 140

Phe Gly Gly Arg Ala Thr Ala Val Phe Asp Ala Ile Gly Asp Gly Gln
145                 150                 155                 160

Asn Gly Asn Asp Cys Asn Gly His Gly Thr His Val Ala Gly Thr Val
                165                 170                 175

Gly Gly Thr Val Tyr Gly Val Ala Lys Ser Val Arg Leu Tyr Ala Val
            180                 185                 190

Arg Val Leu Asn Cys Ser Gly Ser Gly Ser Asn Ser Gly Val Ile Ala
        195                 200                 205

Gly Val Asp Trp Val Arg Gln Asn Ala Arg Arg Pro Ala Val Ala Asn
    210                 215                 220

Met Ser Leu Gly Gly Gly Ala Ser Ser Ala Leu Asp Thr Ala Val Asn
225                 230                 235                 240

Asn Ala Ile Asn Ala Gly Ile Thr Phe Ala Leu Ala Ala Gly Asn Ser
                245                 250                 255

Asn Arg Asp Ala Cys Gln Phe Ser Pro Ala Arg Val Thr Ala Gly Ile
            260                 265                 270

Thr Val Gly Ala Thr Thr Ser Thr Asp Ala Arg Ala Ser Tyr Ser Asn
        275                 280                 285

Tyr Gly Ser Cys Leu Asp Leu Phe Ala Pro Gly Ser Ser Ile Thr Ser
    290                 295                 300

Ala Trp Ile Ser Ser Asp Thr Ser Thr Asn Thr Ile Ser Gly Thr Ser
305                 310                 315                 320

Met Ala Thr Pro His Val Ala Gly Val Ala Ala Leu Tyr Leu Gln Ser
                325                 330                 335

Asn Pro Ser Ala Ser Pro Ala Thr Val Arg Asn Ala Ile Val Gly Asn
            340                 345                 350

Ala Thr Ser Gly Val Val Ser Asn Ala Gly Arg Arg Ser Pro Asn Leu
        355                 360                 365

Leu Leu Tyr Ser Asn Tyr Gly Asn Leu Tyr Phe Gln Ser His His His
    370                 375                 380

His His His His His
385
```

<210> SEQ ID NO 11
<211> LENGTH: 300
<212> TYPE: DNA
<213> ORGANISM: Artificial Sequence
<220> FEATURE:
<223> OTHER INFORMATION: inhibitory domain DNA

<400> SEQUENCE: 11

```
ctagccccgg tgctaggact ggataacccc aacgttatcc aggggcagta cattgtggtc      60

tacaaggatg atgccaacgt gctgcccacc ctgcaaagcc tgaaagccgc tttagatggg     120

ggtgtaaccc ttcagcggga actggaaagc ctggggctgg cacccgacgc cagggttgag     180

caggtttaca ccgctgctct gctggggctt gcggcccggc tatcacccga gaatttagcc     240

gcgctgcggc aggatccccg ggtggcctac atcgaggccg accaggtcat gagcatcagc     300
```

<210> SEQ ID NO 12
<211> LENGTH: 834
<212> TYPE: DNA
<213> ORGANISM: Artificial Sequence
<220> FEATURE:
<223> OTHER INFORMATION: Catalytic Domain_DNA

<400> SEQUENCE: 12

```
gccacccaga ccggtgcgac ctggggcctg gatcgcatag accagcgcac cctacccctc     60

agcggtacct tcacctacag caacacgggc agcggcgtga acgcctacat catcgatacc    120

ggtatccggg tgagccacag cgagtttggc ggtcgggcca cggcggtttt cgacgctatt    180

ggagacggcc agaatggcaa cgactgcaac ggccatggca cccatgtggc tggaacggta    240

ggcggcacgg tctacggcgt agccaaaagc gtgcggttgt acgcggtgcg ggtgcttaat    300

tgcagcggct cgggcagcaa ctcgggcgta attgccgggg tggactgggt gcggcagaat    360

gcccggaggc cagcggtagc caacatgagc ctgggtgggg gggcctcgag cgccctcgat    420

accgcggtca ataacgccat caacgccggg attacctttg ccctggccgc aggtaacagc    480

aaccgcgacg cctgccagtt ctcgccagcc cgcgtcactg caggcattac cgtgggggcc    540

accacctcca ccgacgccag ggcctcctat tccaactacg gtagctgcct cgacctcttc    600

gcccccggct cttccatcac ctcggcctgg attagcagcg acacctcgac caacaccatc    660

agcggaacct cgatggccac cccccatgtg gccggggtag cggctttgta cctgcaaagc    720

aaccccagtg ccagccccgc caccgtgcgc aacgccattg tgggcaacgc cacttcgggt    780

gtggtgagca acgccgggcg gcgttcgccc aacctgctgc tgtacagcaa ttac          834
```

<210> SEQ ID NO 13
<211> LENGTH: 100
<212> TYPE: PRT
<213> ORGANISM: Artificial Sequence
<220> FEATURE:
<223> OTHER INFORMATION: inhibitory domain

<400> SEQUENCE: 13

```
Leu Ala Pro Val Leu Gly Leu Asp Asn Pro Asn Val Ile Gln Gly Gln
1               5                   10                  15

Tyr Ile Val Val Tyr Lys Asp Asp Ala Asn Val Leu Pro Thr Leu Gln
            20                  25                  30

Ser Leu Lys Ala Ala Leu Asp Gly Gly Val Thr Leu Gln Arg Glu Leu
        35                  40                  45

Glu Ser Leu Gly Leu Ala Pro Asp Ala Arg Val Glu Gln Val Tyr Thr
    50                  55                  60

Ala Ala Leu Leu Gly Leu Ala Ala Arg Leu Ser Pro Glu Asn Leu Ala
65                  70                  75                  80

Ala Leu Arg Gln Asp Pro Arg Val Ala Tyr Ile Glu Ala Asp Gln Val
                85                  90                  95

Met Ser Ile Ser
            100
```

<210> SEQ ID NO 14
<211> LENGTH: 278
<212> TYPE: PRT
<213> ORGANISM: Artificial Sequence
<220> FEATURE:
<223> OTHER INFORMATION: catalytic domain

<400> SEQUENCE: 14

```
Ala Thr Gln Thr Gly Ala Thr Trp Gly Leu Asp Arg Ile Asp Gln Arg
1               5                   10                  15

Thr Leu Pro Leu Ser Gly Thr Phe Thr Tyr Ser Asn Thr Gly Ser Gly
            20                  25                  30

Val Asn Ala Tyr Ile Ile Asp Thr Gly Ile Arg Val Ser His Ser Glu
        35                  40                  45
```

-continued

Phe Gly Gly Arg Ala Thr Ala Val Phe Asp Ala Ile Gly Asp Gly Gln
    50                  55                  60

Asn Gly Asn Asp Cys Asn Gly His Gly Thr His Val Ala Gly Thr Val
65                  70                  75                  80

Gly Gly Thr Val Tyr Gly Val Ala Lys Ser Val Arg Leu Tyr Ala Val
                85                  90                  95

Arg Val Leu Asn Cys Ser Gly Ser Gly Ser Asn Ser Gly Val Ile Ala
            100                 105                 110

Gly Val Asp Trp Val Arg Gln Asn Ala Arg Arg Pro Ala Val Ala Asn
        115                 120                 125

Met Ser Leu Gly Gly Gly Ala Ser Ser Ala Leu Asp Thr Ala Val Asn
    130                 135                 140

Asn Ala Ile Asn Ala Gly Ile Thr Phe Ala Leu Ala Ala Gly Asn Ser
145                 150                 155                 160

Asn Arg Asp Ala Cys Gln Phe Ser Pro Ala Arg Val Thr Ala Gly Ile
                165                 170                 175

Thr Val Gly Ala Thr Thr Ser Thr Asp Ala Arg Ala Ser Tyr Ser Asn
            180                 185                 190

Tyr Gly Ser Cys Leu Asp Leu Phe Ala Pro Gly Ser Ser Ile Thr Ser
        195                 200                 205

Ala Trp Ile Ser Ser Asp Thr Ser Thr Asn Thr Ile Ser Gly Thr Ser
    210                 215                 220

Met Ala Thr Pro His Val Ala Gly Val Ala Ala Leu Tyr Leu Gln Ser
225                 230                 235                 240

Asn Pro Ser Ala Ser Pro Ala Thr Val Arg Asn Ala Ile Val Gly Asn
                245                 250                 255

Ala Thr Ser Gly Val Val Ser Asn Ala Gly Arg Arg Ser Pro Asn Leu
            260                 265                 270

Leu Leu Tyr Ser Asn Tyr
        275

<210> SEQ ID NO 15
<211> LENGTH: 90
<212> TYPE: PRT
<213> ORGANISM: Artificial Sequence
<220> FEATURE:
<223> OTHER INFORMATION: alpha factor

<400> SEQUENCE: 15

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu
                85                  90

<210> SEQ ID NO 16
<211> LENGTH: 7
<212> TYPE: PRT
<213> ORGANISM: Artificial Sequence
<220> FEATURE:
<223> OTHER INFORMATION: linker sequence

<400> SEQUENCE: 16

Gly Asn Leu Tyr Phe Gln Ser
1               5

<210> SEQ ID NO 17
<211> LENGTH: 60
<212> TYPE: DNA
<213> ORGANISM: Artificial Sequence
<220> FEATURE:
<223> OTHER INFORMATION: Alpha-amylase signal peptide

<400> SEQUENCE: 17
atggtcgctt ggtggtcttt gtttctgtac ggtcttcagg tcgctgcacc tgctttggct    60

<210> SEQ ID NO 18
<211> LENGTH: 20
<212> TYPE: PRT
<213> ORGANISM: Artificial Sequence
<220> FEATURE:
<223> OTHER INFORMATION: Alpha-amylase signal peptide

<400> SEQUENCE: 18

Met Val Ala Trp Trp Ser Leu Phe Leu Tyr Gly Leu Gln Val Ala Ala
1               5                   10                  15

Pro Ala Leu Ala
            20

<210> SEQ ID NO 19
<211> LENGTH: 54
<212> TYPE: DNA
<213> ORGANISM: Artificial Sequence
<220> FEATURE:
<223> OTHER INFORMATION: Glucoamylase signal peptide

<400> SEQUENCE: 19
atgtctttta gatccttgtt ggctttgtct ggtttggttt gttctggttt ggct    54

<210> SEQ ID NO 20
<211> LENGTH: 18
<212> TYPE: PRT
<213> ORGANISM: Artificial Sequence
<220> FEATURE:
<223> OTHER INFORMATION: Glucoamylase signal peptide

<400> SEQUENCE: 20

Met Ser Phe Arg Ser Leu Leu Ala Leu Ser Gly Leu Val Cys Ser Gly
1               5                   10                  15

Leu Ala

<210> SEQ ID NO 21
<211> LENGTH: 54
<212> TYPE: DNA
<213> ORGANISM: Artificial Sequence
<220> FEATURE:
<223> OTHER INFORMATION: Serum albumin signal peptide

<400> SEQUENCE: 21
atgaagtggg ttacctttat ctctttgttg tttcttttct cttctgctta ctct    54

<210> SEQ ID NO 22
<211> LENGTH: 18
<212> TYPE: PRT

<213> ORGANISM: Artificial Sequence
<220> FEATURE:
<223> OTHER INFORMATION: Serum albumin signal peptide

<400> SEQUENCE: 22

Met Lys Trp Val Thr Phe Ile Ser Leu Leu Phe Leu Phe Ser Ser Ala
1               5                   10                  15

Tyr Ser

<210> SEQ ID NO 23
<211> LENGTH: 48
<212> TYPE: DNA
<213> ORGANISM: Artificial Sequence
<220> FEATURE:
<223> OTHER INFORMATION: Inulinase signal peptide

<400> SEQUENCE: 23
atgaagttag catactcctt gttgcttcca ttggcaggag tcagtgct                48

<210> SEQ ID NO 24
<211> LENGTH: 16
<212> TYPE: PRT
<213> ORGANISM: Artificial Sequence
<220> FEATURE:
<223> OTHER INFORMATION: Inulinase signal peptide

<400> SEQUENCE: 24

Met Lys Phe Ala Tyr Ser Leu Leu Leu Pro Leu Ala Gly Val Ser Ala
1               5                   10                  15

<210> SEQ ID NO 25
<211> LENGTH: 57
<212> TYPE: DNA
<213> ORGANISM: Artificial Sequence
<220> FEATURE:
<223> OTHER INFORMATION: Invertase signal peptide

<400> SEQUENCE: 25
atgcttttgc aagctttcct tttccttttg gctggttttg cagccaaaat atctgca      57

<210> SEQ ID NO 26
<211> LENGTH: 19
<212> TYPE: PRT
<213> ORGANISM: Artificial Sequence
<220> FEATURE:
<223> OTHER INFORMATION: Invertase signal peptide

<400> SEQUENCE: 26

Met Leu Leu Gln Ala Phe Leu Phe Leu Leu Ala Gly Phe Ala Ala Lys
1               5                   10                  15

Ile Ser Ala

<210> SEQ ID NO 27
<211> LENGTH: 78
<212> TYPE: DNA
<213> ORGANISM: Artificial Sequence
<220> FEATURE:
<223> OTHER INFORMATION: Killer virus signal peptide

<400> SEQUENCE: 27
atgactaagc aacccaagt attagttaga tccgtcagta tattattttt catcacatta    60
ctacatctag tcgtagct                                                 78

<210> SEQ ID NO 28

-continued

<211> LENGTH: 26
<212> TYPE: PRT
<213> ORGANISM: Artificial Sequence
<220> FEATURE:
<223> OTHER INFORMATION: Killer virus signal peptide

<400> SEQUENCE: 28

Met Thr Lys Pro Thr Gln Val Leu Val Arg Ser Val Ser Ile Leu Phe
1 5 10 15

Phe Ile Thr Leu Leu His Leu Val Val Ala
20 25

<210> SEQ ID NO 29
<211> LENGTH: 78
<212> TYPE: DNA
<213> ORGANISM: Artificial Sequence
<220> FEATURE:
<223> OTHER INFORMATION: Lysozyme signal peptide

<400> SEQUENCE: 29
atgctgggta agaacgaccc aatgtgtctt gttttggtct tgttgggatt gactgctttg 60
ttgggtatct gtcaaggt 78

<210> SEQ ID NO 30
<211> LENGTH: 26
<212> TYPE: PRT
<213> ORGANISM: Artificial Sequence
<220> FEATURE:
<223> OTHER INFORMATION: Lysozyme signal peptide

<400> SEQUENCE: 30

Met Leu Gly Lys Asn Asp Pro Met Cys Leu Val Leu Val Leu Leu Gly
1 5 10 15

Leu Thr Ala Leu Leu Gly Ile Cys Gln Gly
20 25

<210> SEQ ID NO 31
<211> LENGTH: 57
<212> TYPE: DNA
<213> ORGANISM: Artificial Sequence
<220> FEATURE:
<223> OTHER INFORMATION: Mating factor alpha-1 signal peptide

<400> SEQUENCE: 31
atgagatttc cttcaatttt tactgcagtt ttattcgcag catcctccgc attagct 57

<210> SEQ ID NO 32
<211> LENGTH: 19
<212> TYPE: PRT
<213> ORGANISM: Artificial Sequence
<220> FEATURE:
<223> OTHER INFORMATION: Mating factor alpha-1 signal peptide

<400> SEQUENCE: 32

Met Arg Phe Pro Ser Ile Phe Thr Ala Val Leu Phe Ala Ala Ser Ser
1 5 10 15

Ala Leu Ala

<210> SEQ ID NO 33
<211> LENGTH: 57
<212> TYPE: DNA
<213> ORGANISM: Artificial Sequence
<220> FEATURE:
<223> OTHER INFORMATION: Mating factor alpha-2 signal peptide -continued

```
<400> SEQUENCE: 33

atgaaattca tttctacctt tctcactttt attttagcgg ccgtttctgt cactgct        57


<210> SEQ ID NO 34
<211> LENGTH: 19
<212> TYPE: PRT
<213> ORGANISM: Artificial Sequence
<220> FEATURE:
<223> OTHER INFORMATION: Mating factor alpha-2 signal peptide

<400> SEQUENCE: 34

Met Lys Phe Ile Ser Thr Phe Leu Thr Phe Ile Leu Ala Ala Val Ser
1               5                   10                  15

Val Thr Ala
```